(12) United States Patent
Jiao et al.

(10) Patent No.: US 6,608,066 B1
(45) Date of Patent: Aug. 19, 2003

(54) TISSUE FACTOR ANTAGONISTS AND METHODS OF USE THEREOF

(75) Inventors: Jin-An Jiao, Weston, FL (US); Lawrence K. Luepschen, Miami, FL (US); Esperanza L. Nieves, Newark, DE (US); Hing C. Wong, Weston, FL (US); Dean P. Taylor, Weston, FL (US)

(73) Assignee: Sunol Molecular Corporation, Miramar, FL (US)

( * ) Notice: Subject to any disclaimer, the term of this patent is extended or adjusted under 35 U.S.C. 154(b) by 0 days.

(21) Appl. No.: 09/698,673

(22) Filed: Oct. 27, 2000

Related U.S. Application Data
(60) Provisional application No. 60/161,855, filed on Oct. 27, 1999.

(51) Int. Cl.$^7$ .................. A61K 31/495; A61K 31/17; C07D 241/04; C07D 221/14; C07D 263/52
(52) U.S. Cl. ............ 514/252.12; 514/183; 514/255.04; 514/258; 514/313; 514/373; 514/888; 514/596; 544/358; 544/396; 544/398; 546/101; 546/103; 546/108; 546/152; 546/159; 546/177; 548/217; 548/237
(58) Field of Search .................. 514/183, 256, 514/252.12, 255.04, 373, 588, 596, 313, 252.13; 544/358, 398, 396; 546/101, 103, 108, 152, 159, 177; 548/217, 237

(56) References Cited

FOREIGN PATENT DOCUMENTS

| EP | 0 236 022 | 9/1987 |
|---|---|---|
| WO | WO 94/05328 | 3/1994 |
| WO | WO 96/40921 | 12/1996 |
| WO | WO 98/40408 | 9/1998 |
| WO | 9852898 | * 11/1998 |
| WO | WO 98/52898 | 11/1998 |
| WO | WO 99/03498 | 1/1999 |
| WO | WO 99/48878 | 9/1999 |
| WO | WO 00/18398 | 4/2000 |
| WO | WO 00/77246 A2 | 12/2000 |

OTHER PUBLICATIONS

Marini et al, Chem Abst.:102:119493, "Flunarizine. Chem. and Physiological charac.", Boll.Chim.Farm. 123, 133(1984).*
Nokolova etal,Chem.Abstr.:83:108329, "Pharmacolog. screening of some mono-& disub.piperazine der.II", Tr.Nauc.Kh.–Far.,9,213(1974).*
Hashimoto et al,Chem.Abst.79:20286, Yuki Gosei Kagaku Kyohai Shi,31/1,94(1973).*
Kato H., "PuBMed Abst.:11959688," Reguln . . . functions of Vasc. wall cells by TF., Arterioscler Thromb Vase Biol 2002 Apr. 1;22/4,539–48.*
Kaiser et al, PuBMed Abst.:11772296, "TFPI:an update of Poten . . .", Expert Opin Investig Drugs 2001 Nov;10/11:1925–35.*
Mikdame et al, PuBMed Abst.:1193743, "What's new in antithrombotic treat.", Ann Biol Clin(Paris)2002 Mar–Apr;60/2:131–41.*
Panteleev et al, PuBMed Abst.:11985578, "TFPI: a possible mechanism. . . ", Eur.J.Biochem. 2002 Apr.,269/8, 2016–31.*
Hollister et al, PuBMed Abnst.:8864292, "Immuno.localizationof TFPI–1, a Kiunitz proteinase inhib., in AD", Brain Res. 1996 Jul. 22;728/1:13–9.*
Kreutzberger, Alfred, et al. "Antiinflammatory Agents. Part 4. 1–Aroyl–and 1–aralkylbenzotriazoles", Arch. Pharm. (Weinheim, Ger.) (1979), 312, pp. 806–811.
Vincentini, Chiara B., et al. "Synthesis of 6–substituted imidazo [4,5–c] pyrazole–5thiones", Heterocycles (1995), vol. 41, No. 3, pp. 497–506.
Ishizuki, T., et al. "Synthesis of 2–'2–(8–hydroxyquinolyl) azo!–1–naphthol and its use in the spectrophotometric determination of calcium in potable water", Anal. Chim. Acta (1985), 176, pp. 63–70.
Lifshits, E.B., et al. "Physicochemical and photographic properties of unsymmetrical carbocyanine with a 5–fluorobenzimidazole group" Abstract XP–002179352.
Kudryavskaya, N.V., et al. "Effect of protected components and their solvents forming a protective shell on the sensitzing properties of dyes of different structure, II. Oxa–and thiaoxacarbocyanines", Abstract XP002179402.
Dorokhov, V. A., et al. "Synthesis of functionalized pyrimidine–4–thiones and pyrido'2, 3–d!pyrimidin–5–one derivatives from animals of monoacylketenes", Abstract XP002179403.
Komkov, A. V., et al. "5–Acetyl–6–amino–4–(methylthio)–2–phenylpyrimidine and its use in the synthesis of functionalized pyrido '2,3–d!pyrimidines and pyrimido'4,5–d!pyrimidines", Abstract XP002179404.
Copy of the International Search Report of Int'l Appln. No. PCT/US00/29725 dated Oct. 24, 2001, 13 pages.

* cited by examiner

Primary Examiner—Richard L. Raymond
Assistant Examiner—Sudhaker B. Patel
(74) Attorney, Agent, or Firm—Peter F. Corless; Edwards & Angell, LLP

(57) ABSTRACT

The invention includes pharmaceutically active compounds and methods of treatment and pharmaceutical compositions that utilize or comprise one or more such compounds. Compounds of the invention are particularly useful for treating or prophylaxis of undesired thrombosis.

14 Claims, 2 Drawing Sheets

Table I

IC$_{50}$ Values for FX & FIX Activation and FXa & FVIIa Activity Assays

| Compound Number | IC$_{50}$ in μM | | | |
|---|---|---|---|---|
| | Factor X Activation | Factor Xa Activity | Factor VIIa Activity | Trypsin Activity |
| 1 | 6 | >833 | >833 | >833 |
| 2 | 1.9 | >833 | >833 | >833 |
| 3 | 28.6 | >833 | >833 | >833 |
| 4 | 3.7 | >833 | >833 | >833 |
| 5 | 34 | >833 | >833 | >833 |
| 6 | 15 | >833 | >833 | >833 |
| 7 | 9.5 | >833 | >833 | >833 |
| 8 | 1 | >833 | >833 | >833 |
| 9 | 17.4 | >833 | >833 | >833 |
| 10 | 2.4 | >833 | >833 | >833 |
| 11 | 0.9 | >833 | >833 | >833 |
| 12 | 9.5 | >833 | >833 | >833 |
| 13 | 13.9 | >833 | >833 | >833 |
| 14 | 10 | >833 | >833 | >833 |
| 15 | 8.2 | >833 | >833 | >833 |
| 16 | >100 | >833 | >833 | >833 |
| 17 | 26.4 | >833 | >833 | >833 |
| 18 | 10.9 | >833 | >833 | >833 |
| 19 | 10 | >833 | >833 | >833 | n.d. – not determined

*Figure 2*

TISSUE FACTOR ANTAGONISTS AND METHODS OF USE THEREOF

The present application claims the benefit of U.S. provisional application No. 60/161,855, filed Oct. 27, 1999, incorporated herein by reference.

BACKGROUND OF THE INVENTION

1. Field of the Invention

The present invention relates to pharmaceutically active compounds and pharmaceutical compositions and therapeutic methods that comprise such compounds. Preferred compounds of the invention are useful for the treatment or prophylaxis of undesired thrombosis. The invention has a wide spectrum of applications including use in screening candidate compounds for the treatment or prophylaxis of thrombosis.

2. Background

Blood clotting assists hemostasis by minimizing blood loss. Generally, blood clotting is initiated by vessel damage and requires platelet aggregation, coagulation factors and inhibition of fibrinolysis. The coagulation factors act through a cascade that relates the vessel damage to formation of a blood clot (see generally L. Stryer, *Biochemistry*, 3rd Ed, W. H. Freeman Co., New York; and A. G. Gilman et al., *The Pharmacological Basis of Therapeutics*, 8th Edition, McGraw Hill Inc., New York, pp. 1311–1331).

Tissue factor (TF), an integral membrane protein of 263 amino acids, is responsible for initiating the coagulation protease cascade. Vascular damage exposes blood to tissue factor expressed on subendothelial cell surfaces, leading to the formation of a calcium-dependent, high-affinity complex with the plasma factor VII (FVII) or activated factor VII (FVIIa). Binding to TF promotes rapid proteolytic cleavage of the zymogen FVII to the active serine protease FVIIa by a number of proteases such as factor Xa, or thrombin. TF also functions as an essential cofactor for FVIIa by dramatically enhancing the catalytic efficiency of FVIIa for its protein substrates factors IX and X. TF/VIIa complex activates factors IX (FIX) and X (FX) via limited proteolysis, ultimately leading to thrombin generation and fibrin deposition. Under pathological conditions such as atherosclerosis or following invasive surgical procedures such as microvascular graft, angioplasty, deployment of an implanted device (e.g., a stent, catheter or arteriovenous shunt), or endarterectomy, TF-initiated coagulation can lead to thrombotic disorders that can result e.g. in heart attack, stroke, unstable angina, graft failure or other coronary disorder.

Thrombosis also may accompany various thromboembolic disorders and coagulopathies such as a pulmonary embolism (e.g., atrial fibrillation with embolization, deep vein thrombosis, etc.) and disseminated intravascular coagulation, respectively. Manipulation of body fluids can also result in an undesirable thrombus, particularly in blood transfusions or fluid sampling, as well as procedures involving extracorporeal circulation (e.g., cardiopulmonary bypass surgery) and dialysis.

Certain anti-coagulants have been used to alleviate or avoid blood clots associated with thrombosis. Blood clotting often can be minimized or eliminated by administering a suitable anti-coagulant or mixture thereof, including one or more of a coumarin derivative (e.g., warfin and dicumarol) or a charged polymer (e.g., heparin, hirudin or hirulog). See e.g., Gilman et al., supra, R. J. Beigering et al., *Ann. Hemathol.*, 72:177 (1996); J. D. Willerson, *Circulation*, 94:866 (1996).

Certain antibodies with anti-platelet activity have also been used to alleviate various thromboses. For example, ReoPro™ is a therapeutic antibody that is routinely administered to alleviate various thromboembolic disorders such as those arising from angioplasty, myocardial infarction, unstable angina and coronary artery stenoses. Additionally, ReoPro™ can be used as a prophylactic to reduce the risk of myocardial infarction and angina (J. T. Willerson, *Circulation*, 94:866 (1996); M. L. Simmons et al., *Circulation*, 89:596 (1994)).

However, use of prior anti-coagulants is often associated with side effects such as hemorrhaging, re-occlusion, "white-clot" syndrome, irritation, birth defects, thrombocytopenia and hepatic dysfunction. Long-term administration of anti-coagulants can particularly increase risk of life-threatening illness (see e.g., Gilman et al., supra).

Protein-based agents are potentially safer, but generally are limited to treatment of acute conditions and often are restricted to parenteral administration. Such agents are considered less suitable for long-term therapies for chronic diseases (such as atherosclerosis, a major cause of heart attack) due to the increased probability of immune response to a protein therapeutic, relatively high production cost and/or limited oral bioavailability.

It would thus be desirable to have new anti-coagulant agents. It would be particularly desirable to have new anti-coagulant agents that could be administered over a relatively long period to treat chronic conditions such as atherosclerosis.

SUMMARY OF THE INVENTION

We have now discovered pharmaceutically active compounds and particularly tissue factor (TF) antagonists that have a wide spectrum of uses including use in the treatment and/or prevention of undesired thrombosis. Preferred compounds of the invention specifically block human factor X and IX activation catalyzed by a human tissue factor/factor VIIa complex. Also discovered are methods for treating or preventing thrombosis that use the compounds and compositions disclosed herein.

More particular methods of this invention include administering a therapeutically effective amount of at least one compound or composition of this invention. The compound or composition is typically given to a mammal in need of such treatment such as a human patient who is susceptible to, suffering from, or recovering from undesired thrombosis, or mammal that is suffering from, recovering from or susceptible to other disease or disorder impacted by tissue factor such as cardiovascular disease, cell proliferation disorder, post-operative complication, or an immune disorder. Preferred compounds and compositions may also be used to treat or prevent recognized disorders impacted by various thromboses such as those particular disorders disclosed herein.

The invention also includes methods for blocking or inhibiting tissue factor-dependent activation of factor X and/or factor IX. These methods in general include contacting tissue factor with a TF blocking compound to thereby inhibit formation of a functional complex of factor X or factor IX with tissue factor or TF/VIIA. Preferably the TF blocking compound binds to tissue factor to thereby inhibit formation of the functional complex. Inhibition or prevention of formation of such a complex in accordance with the invention can have quite broad application, including for treatment of the above-mentioned diseases or disorders in mammals, particularly humans suffering from or susceptible to such diseases or disorders.

Preferred compounds of the invention generally exhibit good blocking activity in at least one test for detecting and preferably measuring TF-mediated blood clotting. More particular tests are standard in vitro assays for measuring activity of a specific blood coagulation factor in which the assay is recognized as providing optimal results in the presence of TF or a TF-associated complex such as the human TF/VIIa complex. The TF can be provided in the assay as a recombinant molecule or molecule purified from natural sources depending usually on the specific assay selected.

A more particular in vitro assay detects and measures activity of a specific blood coagulation factor which has a recognized activity enhanced in the presence of human TF or the human TF/VIIa complex. Of preferred interest are standard in vitro assays for measuring TF-dependent activation of factor X to FXa and factor IX to FIXa. Sometimes these assays will be referred to herein as a "primary screening assay" or related term or phrase such as "method of discovery" to denote preferred use of the assay in screening compounds.

For example a particularly preferred compound of the invention will exhibit good blocking activity in the primary screening assay for measuring TF-dependent activation of factor X to FXa. Additionally preferred compounds will exhibit good blocking activity in the primary screening assay for measuring TF-dependent activation of factor IX to FIXa.

It will be appreciated that by the phrase "good blocking activity" or related phrase is meant preferred use of a compound of this invention to reduce or inhibit clotting activation of factor X to FXa and/or factor IX to FIXa. A preferred compound is a synthetic or semi-synthetic compound such as those small molecule compounds disclosed below. More particular disclosure relating to the primary screening assays is provided as follows.

Preferred small molecule compounds of this invention will exhibit an $IC_{50}$ (concentration required to, inhibit factor X activation by about 50% relative to a suitable control) of about 100 $\mu$M or less and preferably about 10 $\mu$M or less. Additionally preferred compounds will exhibit equivalent or greater than about 70% inhibition of TF- or TF/VIIa dependent FX activation in the assay. In a preferred embodiment, the primary screening assay includes all of the following steps:

1) admixing in a suitable assay solution TF/VIIa complex and factor X under conditions conducive to forming factor Xa,
2) contacting the solution with a detectably-labeled factor Xa substrate; and
3) detecting labeled product in the solution as being indicative of the factor X activation.

Preferred use of this primary screening assay effectively measures capacity of a candidate compound to decrease or eliminate TF- or TF/VIIa dependent factor X activation. The assay is generally flexible and can be manipulated as necessary to test a compound for capacity to block factor X activation. For example, the candidate compound can be added at any one or more of the steps shown above with addition of the compound at step 1) being preferred for many screening applications.

A preferred TF/VIIa complex for use in the method includes TF which has been exposed to conditions conducive to exposing good TF blocking sites. More specific conditions for isolating and using the TF are provided below.

As mentioned above, another primary screening assay is a standard in vitro assay for measuring factor IX activation by TF or TF/VIIa. In this example, a preferred compound will exhibit an $IC_{50}$ (concentration required to inhibit factor IX activation in the assay by about 50% relative to a suitable control) in the assay of from between about 200 $\mu$M or less, and preferably about 10 $\mu$M or less. In a preferred embodiment, the standard assay for measuring the factor IX activation includes all of the following steps:

1) admixing in a suitable assay solution TF/VIIa complex with factor IX under conditions conducive to forming factor FIXa,
2) contacting the solution with a detectably-labeled FIXa substrate; and
3) detecting labeled product in the solution as being indicative of the factor IXa activation by TF/VIIa.

In preferred embodiments, this screening assay effectively measures capacity of the candidate compound to decrease or eliminate Factor IX activation. The assay is generally sensitive to TF- or TF/VIIa-dependent formation of FIXa and can be used in several ways to test a desired compound for capacity to block the factor IX activation. For example, a compound to be further tested can be added at one or more of the steps shown above with addition of the compound at step 1) being preferred for most screening applications. Typically preferred compounds of this invention will exhibit good blocking activity in this example of the primary screening assay.

A further preferred primary screen of the invention is the Prothrombin Time (PT) test or assay which measures extrinsic pathway clotting. This test is standard in the field and is routinely used to measure clotting in biological samples such as blood plasma More particularly preferred compounds of this invention will exhibit good inhibitory activity in the PT assay. A typically preferred compound will increase plasma clotting time in the PT assay relative to a suitable control by at least about 5% to about 10% (seconds). Preferred use of the PT assay measures TF-mediated blood plasma clot time and is performed as follows:

1) providing citrated plasma in a suitable assay solution under conditions conducive to plasma coagulation,
2) admixing a suitable tissue factor preparation and calcium in the solution under conditions suitable for initiating plasma clotting; and
3) measuring the clot time in the solution to determine the prothrombin clot time (PT).

Preferred use of the PT assay measures capability of the compound tested to prolong the prothrombin clot time. The PT assay is well known in this field and can be employed in one or a combination of ways to test the compound for capacity or capability to increase or block the prothrombin clot time.

Especially preferred compounds of this invention exhibit good activity in at least one of the primary assays mentioned above (factor X, factor IX activation and/or PT tests).

Good inhibition of the TF- or TF/VIIa-dependent activation in any one or more of the above primary screening assays at least in many cases can be attributed to effects of the compound on TF/VIIa and/or FXa activities. As discussed, preferred compounds of the invention are TF-antagonists and generally exhibit good blocking activity in preferred in vitro assays for measuring TF-mediated blood coagulation. Thus it will usually be desirable to further test compounds giving good blocking activity in one or more of the above primary screening assays and in at least one and preferably more than one of the "secondary screening assays" discussed below. Such secondary assays can facilitate further identification and selection of candidate compounds having desired TF-antagonist activity, e.g., by eliminating from consideration compounds having activity other than desired activity such as compounds impacting protease activity.

A variety of secondary assays can be conducted in accord with this invention to further evaluate compounds identified in a primary assay, e.g. to further evaluate activity identified in a primary assay or to determine the presence of a certain undesired activity. For example, additionally preferred compounds of this invention will exhibit substantially reduced or negligible activity in other secondary screening assays which are not optimized to measure TF-antagonism. That is, these secondary assays may not be TF dependent. Particular examples of such assays include those formatted to measure thrombin, trypsin, or activated factors such as FXa, FIXa, or FVIIa. Also, preferred compounds exhibit negligible activity in an Activated Partial Thromboplastin Time (APTT) test or assay. More specific examples of such secondary screening assays are provided in the discussion and Examples which follow.

In any one or all of the assays disclosed herein including the primary screens and secondary tests discussed above, the candidate compound can be provided in the assay as the sole active agent or it can be combined with other agents to be tested including other compounds or compositions of this invention. In this embodiment, the screening assays are particularly useful for detecting and preferably quantifying synergism between the compounds, agents or compositions.

A variety of inhibitors against human tissue factor are disclosed herein. These compounds can be used in the screening assays described herein as well as the treatment and prevention methods of this invention.

For example, disclosed herein are certain compounds that are sometimes referenced herein as "TF antagonists", "TF blocking compounds" or similar phrase. Preferred compounds of the invention are small molecules and do not include peptides.

Preferred TF antagonists have been disclosed in U.S. application Ser. No. 09/406,269, filed Sep. 24, 1999, and corresponding PCT application number PCT/US99/22238, filed Sep. 24, 1999, both incorporated herein by reference. That application discloses inter alia phosphonate compounds, including aryl-substituted phosphonate compounds.

We have now discovered additional TF antagonist compounds that are useful in the methods of the invention.

More particularly, preferred compounds of the invention include one or more of certain polar groups, particularly carboxy (—COOH), amido (i.e. —C(=O)—N—, either in non-cyclic or cyclic group, and tautomers thereof), thioamido (i.e. —C(=S)—N—, either in non-cyclic or cyclic group, and tautomers thereof), sulfinyl (—S(O))—, sulfonyl (—S(O)$_2$—), sulfono (SO$_3$) or nitro (NO$_2$) groups. Preferred compounds of the invention include such polar groups together with an aromatic moiety, particularly a carbocyclic aryl group such as phenyl, naphthyl and the like, or a heteroaryl group typically having from 1 to 3 separate or fused rings, 5 to 8 atoms per ring and 1–3 hetero (N, O or S) atoms. The invention also includes non-aromatic compounds.

More specifically, preferred compounds of the invention include those of the following Formula I:

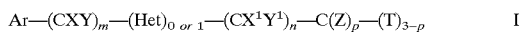

Ar is optionally substituted carbocyclic aryl or optionally substituted heteroaryl;

Het is optionally substituted N, O or S;

each T is independently a polar group such as amido (i.e. —C(=O)—N—, either in non-cyclic or cyclic group, and tautomers thereof), thioamido (i.e. —C(=S)—N—, either in non-cyclic or cyclic group, and tautomers thereof), carboxy, sulfinyl, sulfonyl, sulfonic (SO$_3$), or nitro group;

each X, each Y, each X', each Y' and each Z are each independently hydrogen; halogen; hydroxyl; sulfhydryl; amino; optionally substituted alkyl preferably having 1 to about 12 carbons, more preferably 1 to about 6 carbons; optionally substituted alkenyl preferably having from about 2 to 12 carbon atoms, more preferably about 2 to 6 carbons; optionally substituted alkynyl preferably having from about 2 to 12 carbon atoms, more preferably about 2 to 6 carbon atoms; optionally substituted alkoxy preferably having 1 to about 12 carbon atoms, more preferably 1 to about 6 carbon atoms; optionally substituted alkylthio preferably having from about 1 to 12 carbon atoms, more preferably about 1 to 6 carbon atoms; optionally substituted alkylsulfinyl preferably having from about 1 to 12 carbon atoms, more preferably about 1 to 6 carbon atoms; optionally substituted alkylsulfonyl preferably having from about 1 to 12 carbon atoms, more preferably about 1 to 6 carbon atoms; or optionally substituted alkylamino preferably having from about 1 to 12 carbon atoms, more preferably about 1 to 6 carbon atoms;

m is an integer of from 0 (where the hetero atom is directly substituted on the aryl group) to 4, and preferably is 0, 1 or 2;

n is an integer of from 0 to 4, and preferably n is 1 or 2;

p is 1 (where the compound has two T groups) or 2 (where the compound has a single T group); and pharmaceutically acceptable salts thereof.

Additional preferred compounds include those of the above formula where Ar is a carbocyclic aryl group, particularly phenyl, such as compounds of the following Formula II:

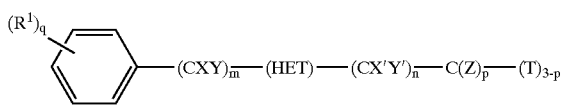

wherein X, Y, Het, T, X', Y', Z, m, and p are the same as defined in Formula I above;

wherein each R$^1$ is independently halogen (F, Cl, Br, I); amino; hydroxy; nitro; carboxy; sulfhydryl; optionally substituted alkyl preferably having 1 to about 20 carbon atoms, more preferably 1 to about 10 carbon atoms, still more preferably 1 to about 6 carbon atoms; optionally substituted alkenyl preferably having 2 to about 20 carbon atoms, more preferably 2 to about 10 carbon atoms, still more preferably 2 to about 6 carbon atoms; optionally substituted alkynyl preferably having 2 to about 20 carbon atoms, more preferably 2 to about 10 carbon atoms, still more preferably 2 to about 6 carbon atoms; optionally substituted alkoxy preferably having 1 to about 20 carbon atoms, more preferably 1 to about 10 carbon atoms, still more preferably 1 to about 6 carbon atoms; optionally substituted alkylthio preferably having 1 to about 20 carbon atoms, more preferably 1 to about 10 carbon atoms, still more preferably 1 to about 6 carbon atoms; optionally substituted alkylsulfinyl preferably having 1 to about 20 carbon atoms, more preferably 1 to about 10 carbon atoms, still more preferably 1 to about 6 carbon atoms; optionally substituted alkylsulfonyl preferably having 1 to about 20 carbon atoms, more preferably 1 to about 10 carbon atoms, still more preferably 1 to about 6 carbon atoms; optionally substituted alkylamino preferably having 1 to about 20 carbon atoms, more preferably 1 to about 10 carbon atoms, still more preferably 1 to about 6 carbon atoms; optionally substituted alkanoyl preferably having 1 to about 20 carbon atoms, more preferably 1 to about 10 carbon atoms, still more preferably 1 to about 6 carbon atoms; optionally substituted carbocyclic aryl; or optionally substituted aralkyl;

q is an integer of from 0 (where the phenyl ring positions are fully hydrogen substituted) to 5, and preferably m is 0, 1 2 or 3; and pharmaceutically acceptable salts thereof.

Of the compounds of the above Formulae I and II, additional preferred compounds include those where the group Het is optionally substituted nitrogen or oxygen, such as compounds of the following Formulae III and IV:

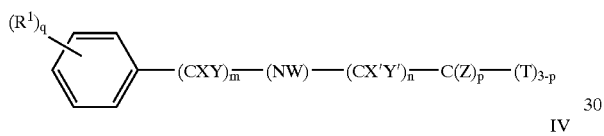

III

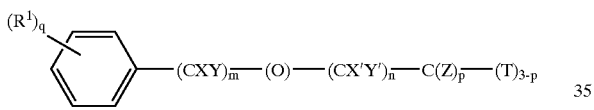

IV wherein in each of Formula III and IV, T, $R^1$, X, Y, X', Y', Z, q, m, n and p are the same as defined in Formulae I and II above; and W is hydrogen, optionally substituted alkyl, preferably having 1 to about 8 carbon atoms, more preferably 1 to about 6 carbon atoms; optionally substituted alkenyl, preferably having 2 to about 8 carbon atoms, more preferably 2 to about 6 carbon atoms; optionally substituted alkynyl, preferably having 2 to about 8 carbon atoms, more preferably 2 to about 6 carbon atoms; optionally substituted alkoxy, preferably having 1 to about 8 carbon atoms, more preferably 1 to about 6 carbon atoms; optionally substituted alkylthio, preferably having 1 to about 8 carbon atoms, more preferably 1 to about 6 carbon atoms; optionally substituted alkylsulfinyl, preferably having 1 to about 8 carbon atoms, more preferably 1 to about 6 carbon atoms; optionally substituted alkylsulfonyl; optionally substituted alkylamino; optionally substituted alanoyl, preferably having 1 to about 8 carbon atoms, more preferably 1 to about 6 carbon atoms; optionally substituted carbocyclic aryl; or optionally substituted aralkyl; and pharmaceutically acceptable salts thereof.

Additional compounds of Formula III include those where the nitrogen group is a direct (no interposed carbon or other atoms) phenyl ring substituent, and particularly preferred compounds of Formula IV include those where the oxygen is a direct ring substituent or a single methylene group is present, such as compounds of the following Formulae IIIa and IVa:

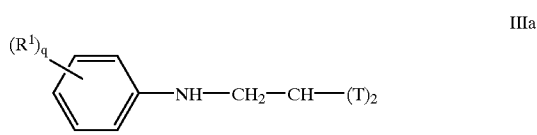

IIIa

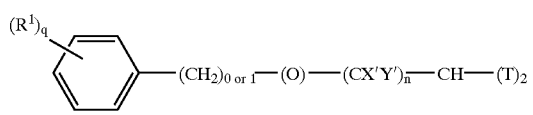

IVa wherein T, R', $X^1$, Y', n and q are the same as defined in Formulae I and II above; and pharmaceutically acceptable salts of those compounds.

Additional preferred compounds of the invention include those that have an optionally substituted amine moiety, such as compounds of the following Formula V:

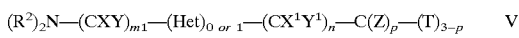

V wherein each of X, Y, Het, X', Y', Z, T, n, g, p are each the same as defined in Formula I above; each $R^2$ is independently hydrogen alkyl, typically $C_{1-8}$ alkyl, aryl, typically carbocyclic aryl such as phenyl or naphthyl, and the like; m1 is an integer of from 0 (where the hetero atom is directly substituted with the amine group) to 4, and preferably is 0, 1 or 2. More preferred compounds according to the Formula V include those in which each of X, Y, X' and Y' is independently hydrogen; Het is 0; Z is a hydroxyl group; and each of m1, n and p is 1. Also included are pharmaceutically acceptable salts of the compound shown in Formula V.

Further preferred compounds of the invention include those that have a polycyclic group of at least two aromatic ring structures. More preferred are compounds having the following Formula VI:

VI wherein each of X, Y, X', Y', Z, n and p is defined as in Formula I above and $Ar^1$ represents a polycyclic aromatic group, preferably an optionally substituted carbocyclic aryl or heteroaryl group having between about 2 to about 3 aromatic rings such as napthyl, acenapthyl and the like, and m2 is an integer of from 0 (where the polycyclic group is directly substituted with the heteroatom) to 4, and preferably is 0, 1, or 2; and pharmaceutically acceptable salts thereof.

Additionally preferred compounds of the Formula VI shown above include those where the $Ar^1$ group represents an optionally substituted biphenyl group, such as those preferred compounds having the following Formula VIa:

VIa wherein $R^1$ is the same as defined above in Formula II; and each of X, Y, X', Y', Z, g, n and p is defined as in Formula I above; m2 is the same as defined above in Formula VI; q1 is an integer from 0 (where the biphenyl group is fully substituted with hydrogen) to 7, and preferably q1 is 0, 1, 2, 3, or 4; and pharmaceutically acceptable salts thereof.

In a more preferred embodiment of the Formula VIa shown above, $Ar^1$ is a substituted biphenyl, $R^1$ is hydroxyl, m2 and n are each 0, Het is a nitrogen atom, Z is hydrogen, p is 1, and q1 is 1, 2 or 3; and pharmaceutically acceptable salts thereof.

Additionally preferred compounds of the invention include alicyclic or heteroalicyclic moiety, such as compounds of the following Formula VII:

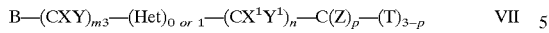

wherein B is an optionally substituted alicyclic or heteroalicyclic group preferably having about 5 to about 8 ring member, and may one or more endocyclic double bonds, provided the ring is not aromatic; each of T, X, Y, X', Y', Z, n and p is defined as in Formula I above, m3 is an integer of from 0 (where the hetero atom is directly substituted with the cyclic hydrocarbon group) to 4, and preferably is 0, 1 or 2; and pharmaceutically acceptable salts thereof.

Additionally preferred compounds include those of the above Formula VII where the B group is preferably cyclopentyl, cyclohexyl, cyclopentenyl, cyclohexenyl, cyclopentadienyl, cyclohexadienyl, cyclopentynyl, or cyclohexynyl such as the compounds of the following Formula VIIa:

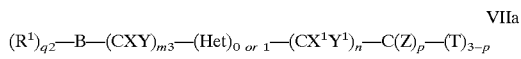

wherein $R^1$ is the same as defined above in Formula II, each of X, Y, X', Y', Z, g, n and p is defined as in Formula I above, m3 is the same as defined above in Formula VIII, and q2 is an integer from 0 (where the B group ring atoms are fully substituted with hydrogen) to 10, and preferably q2 is 0, 1, 2, or 3; and pharmaceutically acceptable salts thereof.

In a more preferred embodiment of the Formula VIIa shown above, $R^1$ is hydroxyl; B is cyclohexyl or cyclopentyl; m3 and n are each 0; g is 1; Het is nitrogen; Z is hydrogen; q2 is 1; p is 2; and pharmaceutically acceptable salts thereof.

Additionally preferred compounds of the invention comprise an imide, such as a succinimide or phthalimide, in addition to a group T as defined above. For instance, preferred imide compounds of the invention include those of the following Formula VIII:

wherein T' and T'' are each the same or different and are the same as defined for T in Formula I above;

D is an optionally substituted imide group such as a succinimide, phthalimide or naphthalic acid imide, optionally with a $C_{1-6}$ alkylene linkage between D and either or both T' or T'' groups; and pharmaceutically acceptable salts thereof.

Particularly preferred compounds of Formula VIII above include those where T' contains an oxygen that is directly linked to a nitrogen of the D group; T'' is carboxyl, sulfinyl or a sulfonic group; q3 and q4 are each 1; and pharmaceutically acceptable salts thereof.

Further preferred compounds of the invention are those of the following Formula IX:

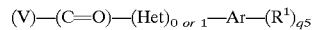

wherein V is a heteroalicyclic or heteroaromatic group having from 1 to 3 separate or fused rings, 5 to about 8 atoms in each ring, and 1–3 hetero (N, O or S) atoms in each ring; Ar, Het are each the same as defined above in Formula I; $R^1$ is the same as defined above in Formula II; q5 is an integer from 0 (in which instance the Ar group is fully substituted with hydrogen) to 5, and preferably q5 is 0, 1, 2, or 3; and pharmaceutically acceptable salts thereof.

Particularly preferred compounds of Formula IX include those where V is an optionally substituted furan, isoxazolyl, pyrole, imidazolyl, pyrazolyl, thienyl, isothiazolyl, furazanyl, or triazobenzene group; and/or Het is oxygen, if present.

Still further preferred compounds of the invention include those of the following Formula IXa, IXb, IXc, and IXd:

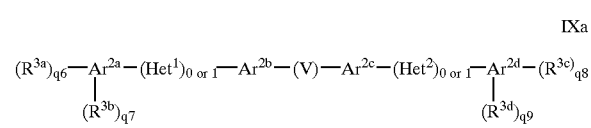

wherein each of $R^{3a}$, $R^{3b}$, $R^{3c}$ and $R^{3d}$ is the same as the $R^1$ group defined in Formula II above with the proviso that each of $R^{3a}$, $R^{3b}$, $R^{3c}$ and $R^{3d}$ can be the same or different; $Het^1$ and $Het^2$ are each independently N, O or S the same or different; each of $Ar^{2a}$, $Ar^{2b}$, $Ar^{2c}$, and $Ar^{2d}$ is independently an optionally substituted carbocyclic aryl or optionally substituted heteroaryl group the same or different; V is the same as defined in Formula IX above; q6 is an integer from 0 (in which case the $Ar^{2a}$ group is hydrogen substituted) to 5, and preferably q6 is 0, 1, 2 or 3; q7 is the same as q6 with the proviso that q6+q7 is not greater than 5; q8 is an integer from 0 (in which case the $Ar^{2b}$ group is hydrogen substituted) to 5, and preferably q8 is 0, 1, 2 or 3; q9 is the same as q8 with the proviso that q7+q8 is not greater than 5; and pharmaceutically acceptable salts thereof.

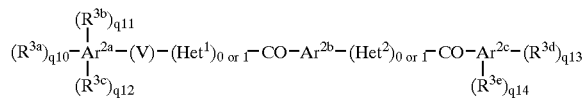

wherein $R^{3e}$ is the same as the $R^1$ group defined in Formula II above, with the proviso that each of $R^{3a}$, $R^{3b}$, $R^{3c}$, $R^{3d}$ and $R^{3e}$ is the same or different; q10 is an integer from 0 (in which case the $Ar^{2a}$ group is hydrogen substituted) to 5, and preferably q is 0, 1, 2 or 3; q11 and q12 are each independently the same as q10 defined above with the proviso that q10+q11+q12 is not be greater than 5; q13 is an integer from 0 (in which case the $Ar^{2c}$ group is hydrogen substituted) to 5, and preferably q13 is 0, 1, 2 or 3; q14 is the same as q13 defined above with the proviso that q13+q14 is not greater than 5; and pharmaceutically acceptable salts thereof.

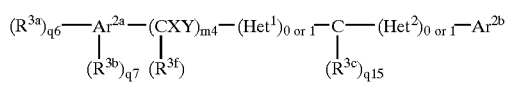

wherein $R^{3f}$ is the same as $R^1$ as defined above in Formula II with the proviso that $R^{3f}$ can also be an optionally substituted cycloalkyl group having from about 5 to about 8 carbons, preferably about 5 to about 6 carbons, and $R^{3f}$ can be the same or different from each of $R^{3a}$, $R^{3b}$, and $R^{3c}$ as defined above; q7 is an integer from 0 (in which case the $Ar^{2a}$ group is hydrogen substituted) to 5, and preferably q7 is 0, 1, 2 or 3 with the proviso that q6+q7 in Formula IXc is not greater than 5; q15 is an integer from 0 (in which instance the carbon atom is bound to hydrogen) to 2; m4 is an integer from 0 (in which case the $Ar^{2a}$ group is substituted with $Het^1$ or the (CXY) group is substituted with a carbon atom bound to the $Ar^{2a}$, $Het^1$, and $R_{3f}$ groups) to 4, and preferably 0, 1, or 2; and pharmaceutically acceptable salts thereof.

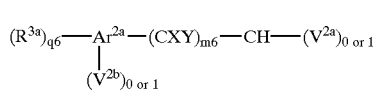

wherein each of ($V^{2a}$) and ($V^{2b}$) is independently the same as V defined above in Formula IXd with the proviso that each of ($V^{2a}$) and ($V^{2b}$) can be the same or different and with the proviso that both $V^{2a}$ and $V^{2b}$ are not both 0; m6 is an integer from 0 (in which case the $Ar^{2a}$ group is directly bound to the —CH— group) to 4, and preferably 0, 1, or 2; and pharmaceutically acceptable salts thereof.

Particularly preferred compounds of Formula IXa above include those compounds in which V includes a pyridyl, pyrazinyl, pyrimidinyl, or triazine ring substituted with an optionally substituted carbocyclic aryl or optionally substituted heteroaryl, preferably a phenyl group.

Particularly preferred compounds of Formula IXb above include those where $Ar^{2a}$, $Ar^{2b}$ and $Ar^{2c}$ are each substituted phenyl; V is an optionally substituted 4- or 5-pyrazolone group; each of q10, q11, q12 and q13 is 1; each of $Het^1$ and $Het^2$ is a nitrogen atom; $R^{3a}$, $R^{3b}$, and $R^{3c}$ are each halogen, preferably chlorine; and each $R^{3d}$, $R^{3e}$ is an —$NO_2^+$ group; and pharmaceutically acceptable salts thereof.

Particularly preferred compounds of Formula IXc above include those where $Ar^{2a}$ and $Ar^{2b}$ are each phenyl, $R^{1f}$ is an optionally substituted cyclopentyl or cyclohexyl group, each of q1, q2, q3, q4, q5, q6 is 1, each of $Het^1$ and $Het^2$ is a nitrogen atom, X and Y are both hydrogen; m, m1 and m2 are each 1, $R^{1a}$, $R^{1b}$, and $R^{1e}$ are each hydroxyl; and pharmaceutically acceptable salts thereof.

Particularly preferred compounds of Formula IXd above include those where $Ar^{3a}$ is substituted phenyl; and $R^{3a}$ is halogen, preferably bromine; X and Y are both hydrogen; m6 is 1; each of $V^{1a}$ and $V^{1b}$ include at least one nitrogen atom, preferably an indolyl, isoindolyl, indazolyl, benzimdazole, or a triazobenzene group; and pharmaceutically acceptable salts thereof.

Still additional preferred TF antagonist compounds of the invention include both aromatic and alicyclic groups, such as compounds of the following Formula X:

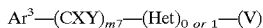

wherein $Ar^3$ is an optionally substituted carbocyclic aryl or heteroaryl group, preferably an optionally substituted quinoline group; each of X, Y, and Het is the same as defined above in Formula I with the proviso that X and Y can also join together to form a carbonyl group; m7 is an integer from 0 (in which case $Ar^3$ is directly bound to Het) to 4, and preferably is 0, 1, or 2; V is the same as defined above in Formula IXa; and pharmaceutically acceptable salts thereof.

The invention also includes phosphonate compounds that do not include aromatic substitution. Such phosphonate compounds also have been disclosed in U.S. application Ser. No. 09/406,269, filed Sep. 24, 1999, as discussed above. Preferred non-aromatic phosphonate compounds will have one, two or three phosphonate groups (i.e. $PO_3$), and 3, 4, 5 or 6 to about 25 carbon atoms, as non-cyclic and/or alicyclic moieties with one or more non-aromatic double or triple carbon-carbon double or triple bonds, typically zero, one two or three carbon-carbon double or triple bonds. The compounds also may contain one or more hetero atoms (N, O or S), typically, zero, one, two or three such hetero atoms. For example, as disclosed in said U.S. application Ser. No. 09/406269, alendronic acid (Fosamax) is an effective TF antagonist compound.

Preferred compounds of the invention also include nitrogen ring compounds, particularly nitrogen ring compounds that contain at least one additional hetero atom (N, O or S), typically one such additional hetero atom and the other ring members being carbon. Typically, the ring compound will be non-aromatic, although it may include one or more additional separate or fused rings that may be aromatic or non-aromatic. Typically, the nitrogen-containing ring will have 5 to about 10 ring atoms, more typically 5, 6, 7, or 8 ring atoms, even more typically 5 or 6 ring atoms. Such nitrogen ring compounds include those of the following Formula XI:

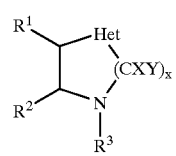

wherein $R^1$, $R^2$, $R^3$, X and Y each may be independently the same as defined for $R^1$ of Formula II above; or $R^1$ and $R^2$ of this Formula XI may be taken together to form a fused carbocyclic aryl (e.g. phenyl or naphthyl), alicyclic (e.g. cyclohexyl), heteroalicyclic or heteroaromatic group having 1–3 fused or separate rings. The heteroalicyclic and heteroaromatic groups will have suitable heteroaromatic or heteroaryl groups will have 1 to 3 rings, 3 to 8 ring members in each ring and from 1 to about 3 hetero atoms (N, O or S), and include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, and benzothiazol;

Het is oxygen, optionally substituted N, S, S(O) or $S(O)_2$, and preferably is oxygen;

X is 1 (5-membered ring), 2 (6-membered ring), 3 (7-membered ring), or 4 1 (8-membered ring); and pharmaceutically acceptable salts thereof.

Preferred compounds of the invention also include substituted piperazine compounds, such as compounds of the following Formula XII:

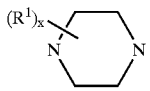

XII wherein each $R^1$ is independently the same as defined for $R^1$ of Formula II above;

x is an integer of from 1 to 10; and pharmaceutically acceptable salts thereof

Additional compounds of the invention bind tissue factor (TF) so that FX does not effectively bind to the TF/factor VIIa complex whereby FX is not effectively converted to its activated form (FXa). Preferred compounds of the invention can inhibit TF function by effectively blocking FX binding access to TF molecules. References herein to "compounds of the invention" are inclusive of compounds of Formulae I through XII.

In preferred aspects, the invention provides methods for inhibiting blood coagulation and blood clot formation in a mammal, methods for inhibiting thrombin generation in a mammal, and methods for treating or preventing thromboembolic disorders in a mammal. The methods of the invention in general comprise administering to a mammal, such as a primate particularly a human, a therapeutically effective amount of a compound of the invention.

Compounds of the invention are particularly useful to alleviate various diseases impacted by tissue factor (TF). By the term "impacted" is meant that the severity or duration of the disease is increased by presence of the TF according to the recognized assays or tests. Particular diseases include thromboses, especially to prevent or inhibit restenosis, or other thromboses following an invasive medical procedure such as arterial or cardiac surgery (e.g., angioplasty), including for prophylaxis of deep vein thrombosis associated with orthopedic or other surgery. Compounds of the invention also can be employed to reduce or even effectively eliminate blood coagulation arising from use of medical implementation (e.g., a catheter, stent or other medical device). Compounds of the invention also will be useful for prophylaxis for long term risk for myocardial infarction. Compounds of the invention also will be useful for treatment of thrombotic conditions that may be associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis.

Additional uses for the present compounds include use in the prevention and treatment of atherosclerosis, inflammation, and as an anti-angiogenic agent, especially to treat cancers, particularly solid cancers such as cancers residing in the lung, breast, liver, brain or other tissue.

Compounds of the invention also can be employed as an anti-coagulant in extracorporeal circulation of a mammal, particularly a human subject. In such methods, one or more compounds of the invention is administered to the mammal in an amount sufficient to inhibit blood coagulation prior to or during extracorporeal circulation such as may be occur with cardiopulmonary bypass surgery, organ transplant surgery or other prolonged surgeries.

Compounds of the invention also can be employed in in vivo diagnostic methods including in vivo diagnostic imaging of a patient.

Compounds of the invention also can be used in in vitro assays, e.g. to selectively inhibit Factor X activation. Such assays of the invention will be useful to determine the presence or likelihood of a patient having blood coagulation or a blood clot.

Pharmaceutical compositions also are provided comprising an effective amount of one or more compounds of the invention and a pharmaceutically acceptable carrier.

Other aspects of the invention are discussed infra.

BRIEF DESCRIPTION OF THE DRAWINGS

FIG. 2 (Table I) shows test data for various compounds of the invention.

DETAILED DESCRIPTION OF THE INVENTION

Figure 1:
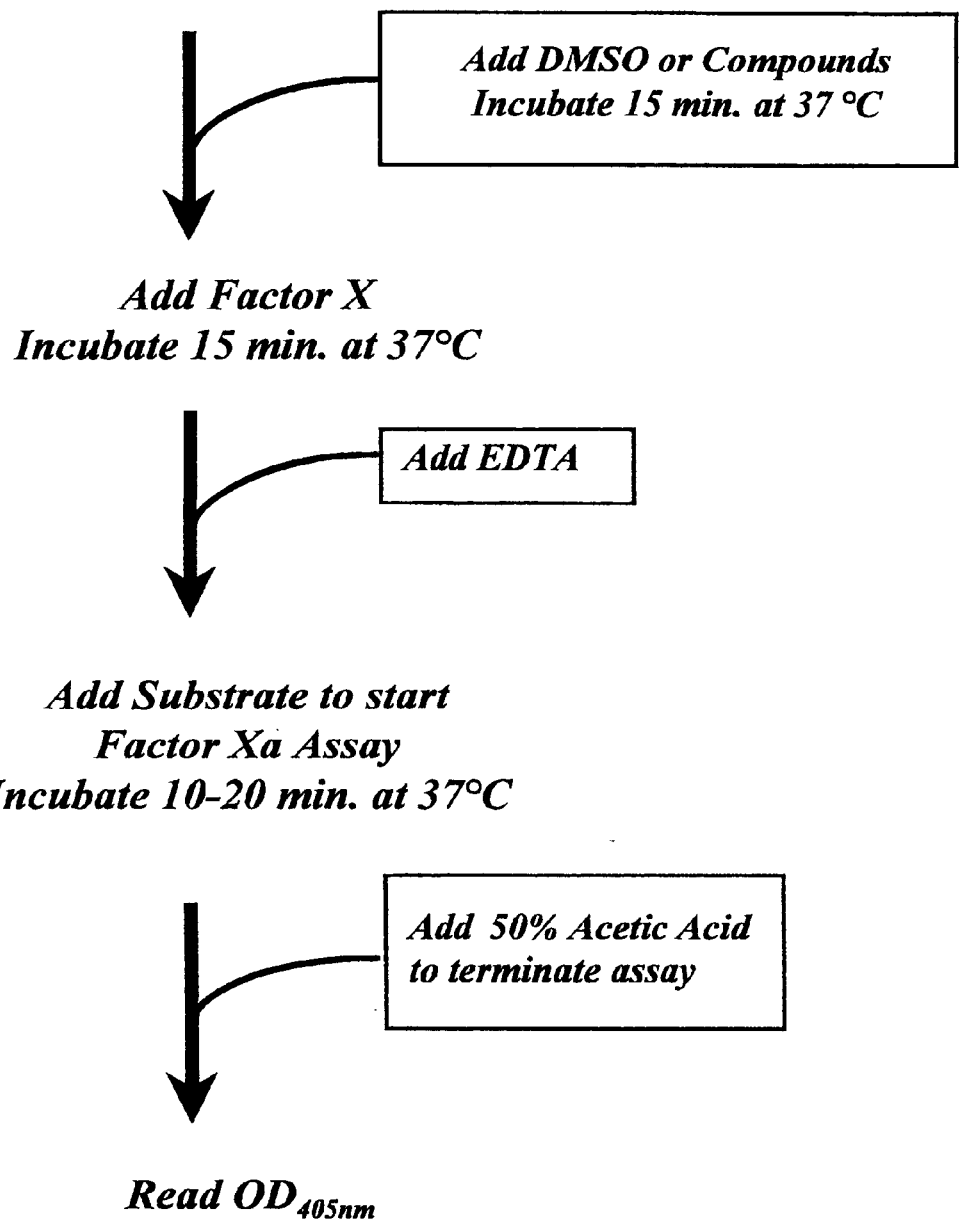
FIG. 1 is a flow chart of a screening assay employed in examples below.

As discussed, the present invention features compounds such as pharmaceutically active compounds and especially pharmaceutical compositions that utilize or comprise one or more of such compounds. Preferred compounds are effective TF antagonists as determined by standard in vitro screening assays disclosed herein. Especially preferred compounds are very useful for the treatment or prophylaxis of undesired thrombosis. The invention has a wide spectrum of applications including use in screening candidate compounds having significant TF-antagonistic activity.

As discussed, preferred compounds and compositions of this invention are good TF antagonists that exhibit significant blocking activity in at least one of and preferably all of the primary screening assays (TF- or TF/VIIa-dependent activation of factor X or factor IX, and PT assay). Especially preferred compounds do not exhibit significant blocking activity in the Activated Partial Thromplastin Time (APTT) assay discussed previously. Further preferred are those compounds of this invention showing insignificant activity in other secondary assays such as those for measuring trypsin, thrombin, factor Xa, factor IXa, and factor VIIa activity as discussed below.

The standard in vitro assays disclosed herein are well-known in the field and are generally flexible. Moreover, the assays can be conveniently manipulated to detect and quantify TF-antagonistic activity as needed. The assays are typically compatible with testing compounds or compositions of this invention in the presence of other therapeutic or experimental agents giving good anti-platelet, anti-thrombolytic, or anti-coagulant activity. In addition, the assays can be used to test effects with recognized anti-TF antibodies. In these embodiments, the standard in vitro assays are especially useful for detecting and preferably measuring significant co-operative or synergistic effects exhibited by the compounds or compositions of this invention.

A more particular example of the primary screening assay discussed previously is as follows. The assay is standard for measuring TF/VIIa-dependent factor X activation. A preferred compound exhibits an $IC_{50}$ in the assay of less than about 100 μM and preferably less than about 10 μM exemplifying good blocking activity in this assay. In a more preferred embodiment, the primary screening preferably includes the following steps.

1) admixing in a suitable assay solution about 0.1 nM of human recombinant TF/VIIa complex (lipidated), about 180 nM human FX, and between from about 0.5 μl to about 10 μl of at least one compound to be tested (optionally dissolved in an appropriate vehicle such as water or dimethylsulfoxide (DMSO)) and incubating the reaction at 37° C. for a few minutes up to about an hour or more, 2) contacting the solution with a suitable chelating agent such as ethylenediaminetetra acetic acid (EDTA) to stop factor X activation, 3) contacting the solution with a detectable amount of a chromogenic substrate specific for FXa (e.g., Spectrozyme FXa or S-2765) and incubating same at 37° C.; and 4) detecting chromophore produced in the solution as being indicative of the factor X activation.

Reference herein to a "standard assay for measuring TF/VIIa-dependent factor X activation" or similar phrase will preferably refer to the above steps 1)–4). More specific disclosure relating to the assay can be found in Example 1 below in which the standard assay for measuring TF/VIIa-dependent factor X activation is specifically adapted for spectrophotometric detection of FXa produced chromophores at 405 nm.

A preferred TF/VIIa complex for use in the method includes TF that has been exposed to conditions suitable for exhibiting good TF blocking sites. Such TF molecules can be obtained by one or a combination of approaches. In one method, human TF is obtained from an overproducing immortalized cell line or an acetone powder derived from human brain. TF is preferably isolated in the presence of at least one non-ionic detergent such as TRITON® X-100 (polyoxyethylene (10) isooctylphenyl ether) under moderate conditions of salt and pH, e.g., 100 mM NaCl and pH 8.0. Preferred amounts of the non-ionic detergent will vary depending on intended use but will generally be in an amount of from between about 0.05% to about 0.5% (w/v). See the Example 1 below for more specific information about isolating human TF.

Additionally preferred TF is exposed to conditions in the standard assay for measuring TF/VIIa-dependent factor X activation. See Example 1 below for more specific disclosure about that standard assay.

Additionally preferred compounds of this invention exhibit good blocking activity in the other primary screening assay for measuring TF/VIIa-dependent factor IX activation. Preferred compounds exhibit an $IC_{50}$ in the assay of less than about 200 $\mu$M with preferably less than about 10 $\mu$M exemplifying good blocking activity in this assay. In a more particular embodiment, the standard assay preferably includes the following steps:

1) admixing in a suitable assay solution about 0.7 nM TF/VIIa complex with 300 nM factor IX and 1000 nM factor X, and from between about 0.5 $\mu$l to about 10 $\mu$l of at least one compound to be tested (optionally dissolved in an appropriate vehicle such as water or dimethylsulfoxide (DMSO)) and incubating the solution at 37° C. from between about a few minutes up to about an hour under conditions suitable for forming FIXa and FXa;

2) contacting the solution with a suitable chelating agent such as EDTA to stop FIX activation;

3) contacting the solution with a chromogenic substrate specific for the FXa (e.g., Spectrozyme FXa) and incubating same at 37° C.; and 4) detecting chromophore in the solution as being indicative of the factor IX activation.

Reference herein to a "standard assay for measuring TF/VIIa dependent factor IX activation" or similar term; or phrase will specifically refer to the above steps 1)–4). See Example 1 below for a more specific illustration of the standard assay adapted for spectrophotometric detection of preferred chromophore at 405 nm.

As discussed, additionally preferred compounds of this invention exhibit good clot time inhibition in the PT assay, preferably an increase in clotting time from between about 20% to at least 100%, and more preferably from between about 20% to at least 500% relative to a suitable control. Clot times are generally measured in seconds. Preferred PT assays are typically performed by adding a suitable amount (e.g. about 1 to 3 nM) of lipidated tissue factor to an assay solution that includes conventionally citrated plasma. The PT assay measures TF-mediated blood plasma clot time and is preferably performed by conducting the following steps:

1) providing about 0.1 ml of citrated human plasma in a suitable assay solution, and combining same with between from about 0.5 $\mu$l to 10 $\mu$l of at least one compound to be tested (optionally dissolved in vehicle such as water or dimethylsulfoxide (DMSO)) and incubating same at room temperature for about 3 to 10 minutes, 2) admixing into the solution from between about 0.2 ml (ca. 1–3 nM recombinant human tissue factor) and about 5–10 mM of calcium to initiate plasma clotting; and 3) measuring the plasma clot time to determine the prothrombin clot time (PT).

Reference herein to a "standard PT assay" or similar phrase or term will specifically refer to the above steps 1)–3). See also *Williams Hematology*, $5^{th}$ Ed. (Beutler, E. et al. Eds.) McGraw-Hill, Inc. Health Professions Div., New York, for more specific disclosure relating to conducting the PT assay.

As mentioned, the present invention provides a variety of assays for detecting and preferably measuring capability of preferred compounds of this invention to antagonize good TF activity. As has also been discussed, certain standard in vitro screening assays are sometimes referred to herein as "secondary screening assays" to denote preferred use with one or more or all of the primary screening assays mentioned previously. Practice of such particular secondary screening assays in conjunction with one or more of the primary screening assays will provide a wide spectrum of useful compounds featuring good anti-TF activity.

Secondary screening assays are disclosed herein and include those optimized to detect and preferably measure the catalytic activities of factor VIIa (FVIIa), factor IXa (FIXa), factor Xa (FXa), thrombin, trypsin, or Russell's viper venom (RVV). In most instances, optimal practice of these assays does not require added TF. Preferred compounds of this invention are specific TF-antagonists and will generally exhibit substantially reduced or negligible activity in these assays. Practice of the secondary screening tests in conjunction with the primary and preferred secondary screening assays discussed previously will facilitate selection of preferred compounds exhibiting highly specific anti-TF activity. Reference herein to "reduced" or "negligible" activity with respect to these secondary screening assays is meant to denote between from about 2% to about 10% of the activity exhibited by a suitable control such as water or DMSO.

As discussed above, the invention provides a wide spectrum of pharmaceutically active compounds and compositions that are useful to treat or prevent undesired thrombosis. Preferred compounds are tissue factor (TF) antagonists and preferably can specifically block human factor X and IX activation catalyzed by human tissue factor/factor VIIa complex. Illustrative compounds of the invention include compounds as described above, including in the above formulae.

In the above formulae, halogen substituent groups of compounds of the invention (which includes e.g. compounds of Formulae I through XII, inclusive of "sub" formulae IIIa, IVa, VIa, VIIa, IXa, IXb, IXc, IXd, as those formulae are defined above) are F, Cl, Br and I. As used herein, the term alkyl unless otherwise modified refers to both cyclic and noncyclic groups, although cyclic groups will comprise at least three carbon ring atoms. Alicyclic alkyl groups are generally preferred. Alkenyl and akynyl groups of compounds of the invention have one or more unsaturated linkages, typically 1 to about 3 or 4 unsaturated linkages. Also, the terms alkenyl and alkynyl as used herein refer to both cyclic and noncyclic groups, although straight or branched noncyclic groups are generally more preferred. Alkoxy groups of compounds of the invention have one or more oxygen linkages, typically 1 to about 5 or 6 oxygen linkages. Alkylthio groups of compounds of the invention have one or more thioether linkages, typically 1 to about 5 or 6 thioether linkages. Alkylsulfinyl groups of compound of the invention have one or more sulfinyl (SO) linkages, typically 1 to about 5 or 6 sulfinyl linkages. Alkylsulfonyl groups of compounds of the invention have one or more sulfonyl ($SO_2$) linkages, typically 1 to about 5 or 6 sulfonyl linkages. Preferred alkylamino groups of compounds of the invention include those groups having one or more primary, secondary and/or tertiary amine groups, preferably 1 to about 3 or 4 amine groups. Suitable alkanoyl groups have one or more carbonyl groups, typically 1 to about 4 or 5 carbonyl groups. Alkoxy, alkylthio, alkylsulfinyl, alkylsulfonyl, alkanoyl and other groups may be suitably either linear or branched. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S). Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, and benzothiazol.

As discussed above, various substituent groups of compounds of the above formulae may be optionally substituted. Suitable groups that may be present on a "substituted" moiety include e.g. halogen such as fluoro, chloro, bromo and iodo; cyano; hydroxyl; nitro; azido; sulfhydryl; alkanoyl e.g. $C_{1-6}$ alkanoyl group such as acetyl and the like; carboxamido; alkyl groups including those groups having 1 to about 12 carbon atoms, preferably from 1 to about 6 carbon atoms; alkenyl and alkynyl groups including groups having one or more unsaturated linkages and from 2 to about 12 carbon atoms, preferably from 2 to about 6 carbon atoms; alkoxy groups having one or more oxygen linkages and from 1 to about 12 carbon atoms, preferably 1 to about 6 carbon atoms; aryloxy such as phenoxy; alkylthio groups including those moieties having one or more thioether linkages and from 1 to about 12 carbon atoms, preferably from 1 to about 6 carbon atoms; alkylsulfinyl groups including those moieties having one or more sulfinyl linkages and from 1 to about 12 carbon atoms, preferably from 1 to about 6 carbon atoms; alkylsulfonyl groups including those moieties having one or more sulfonyl linkages and from 1 to about 12 carbon atoms, preferably from 1 to about 6 carbon atoms; aminoalkyl groups such as groups having one or more N atoms and from 1 to about 12 carbon atoms, preferably from 1 to about 6 carbon atoms; carbocyclic aryl having 6 or more carbons, particularly phenyl; aryloxy such as phenoxy; aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofiranyl, tetrahydropyranyl, piperidinyl, morpholino and pyrrolidinyl. A "substituted" R', W, X, Y and Z substituent, or other substituent of a compound of the invention may be substituted at one or more available positions, typically 1, 2 or 3 positions, by one or more suitable groups such as those listed immediately above.

Specifically preferred compounds of the invention include the compounds 1 through 19 (compound number designations immediately below the depicted structures), and pharmaceutically acceptable salts of those compounds. Those compound designations are used elsewhere in the present disclosure, and refer to the specified compounds of the structures shown immediately below.

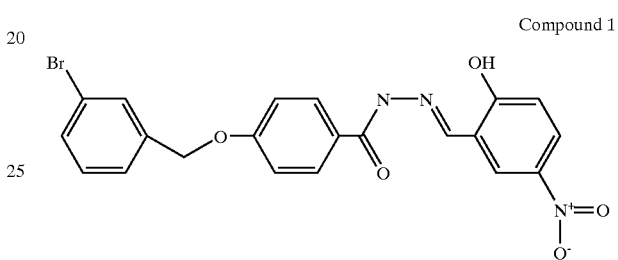

Compound 1

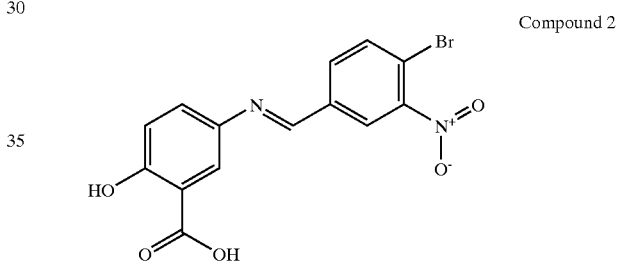

Compound 2

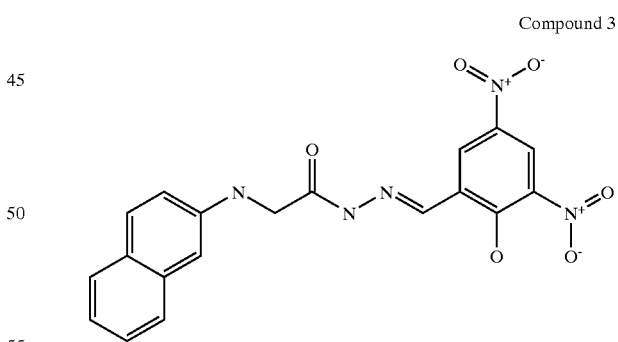

Compound 3

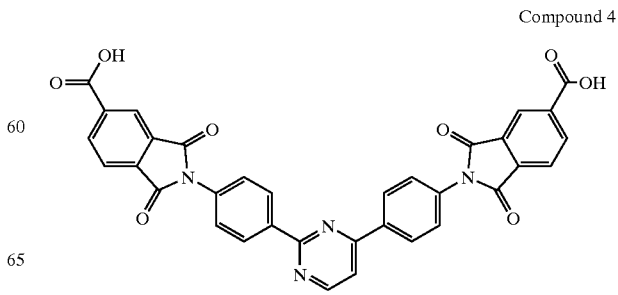

Compound 4

Compound 5
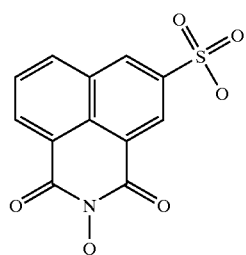
Compound 6
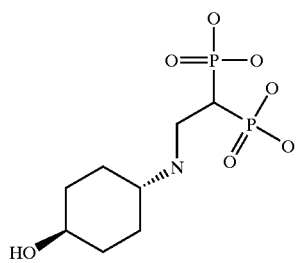
Compound 7
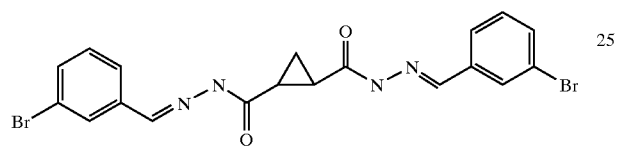
Compoune 8
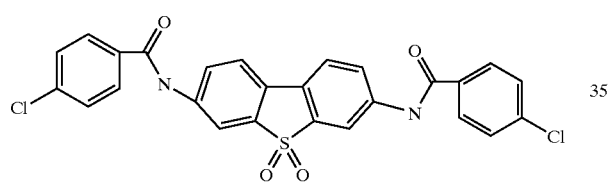
Compound 9
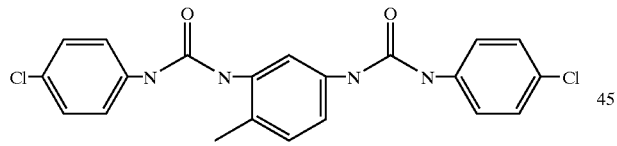
Compound 10
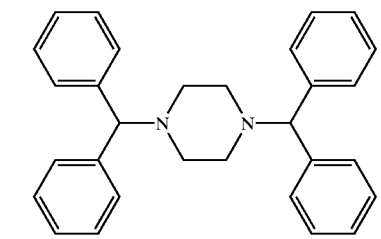
Compound 11
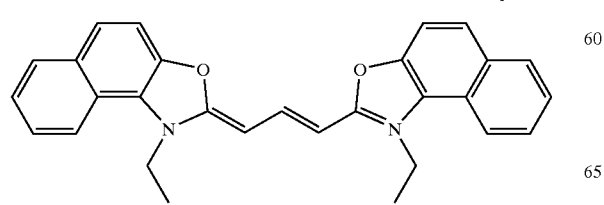
Compound 12
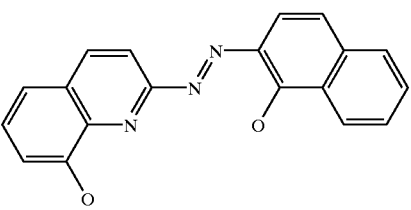
Compound 13
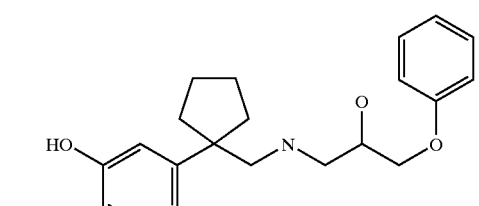
Compound 14
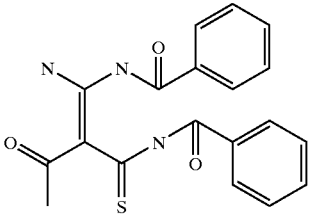
Compound 15
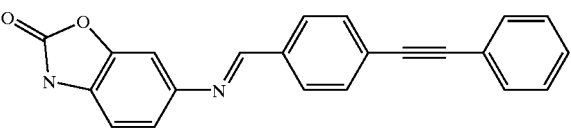
Compound 16
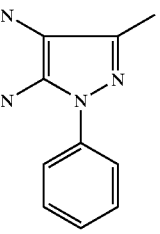
Compound 17

-continued

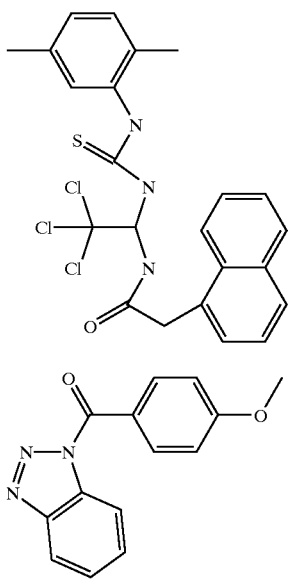

Compound 18

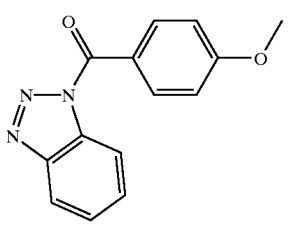

Compound 19

Compounds of the invention can be prepared by procedures generally known in the art. See March, *Advanced Organic Chemistry*, (4th Ed., 1992). For instance, compounds of Formulae I through IV (inclusive of Formulae IIIA and IVA) can be synthesized by appropriate substitution with the polar group of the aromatic compound, e.g. substitution of a phenolic, aniline or benzylic compound, or other substituted aromatic compound having e.g. an electrophilic group suitable for a substitution reaction. Other compounds of the invention can be similarly prepared. For example, imide compounds of Formula VIII can be synthesized by straightforward substitution of commercially available compounds.

Reference herein to a "TF blocking compound," "TF antagonist" or related term generally includes those compounds disclosed herein exhibiting good blocking activity in at least one of the primary screening assays such as the FX activation assay or the PT assay. More particular TF blocking compounds specifically bind TF. Without wishing to be bound to theory, the compounds are believed to block FX or FIX from binding TF in a way sufficient to reduce or block activation to FX or FIX, respectively.

Reference to a "therapeutically effective amount" of a composition is such as to produce a desired effect in a host such as a mammal and especially a primate such as a human patient. Preferably the effect can be monitored using several end-points known to those of skill in the field. For example, one desired effect is an increase or stabilization of cardiovascular function as measured, e.g., by enhanced heart function and especially blood flow within subject vessels. Such impact can be monitored and usually measured in terms of a therapeutic effect, e.g., improved cardiovascular function, alleviation of one or more symptoms indicative of compromised heart function or function of related vasculative, or other particularized physiological assays. These specific methods are not intended to be inclusive and further methods intended to suit a specific application such as thrombin, cancer, or atherosclerosis will be apparent to the skilled worker in the field.

As discussed above, a compound of the invention can be administered to a mammal, preferably a primate such as a human, to prevent or reduce thromboses. Therapies in which compounds of the invention will be useful include treatment or prophylaxis of venous thrombosis and pulmonary embolism, arterial thrombosis e.g. myocardial ischemia, myocardial infarction, unstable angina, stroke associated with thrombosis, and peripheral arterial thrombosis. Compounds of the invention also may be useful for treatment or prophylaxis of atherosclerotic diseases e.g. coronary arterial disease, cerebral arterial disease and peripheral arterial disease. Compounds of the invention also will be useful for anticoagulation treatment involving artificial organs, cardiac valves, medical implementation (e.g. an indwelling device such as a catheter, stent, etc.) and the like. Compounds of the invention also will be useful for therapy in other disorders or diseases where blood coagulation may be involved as a related disorder, e.g cancer, inflammatory diseases particularly arthritis, and diabetes.

One or more TF antagonist compounds also may be administered as the sole therapeutic agent(s) in a particular protocol, or the compound(s) of the invention may be administered together with other therapeutic agents, e.g. a pharmaceutical targeted for interaction in the blood clotting mechanism such as streptokinase, tPA, urokinase and other agents that lyse clots. A compound of the invention also can be administered with other agents such as one or more other anti-coagulants (e.g., heparin, hirudin, or hirulog), or an anti-platelet (e.g., ReoPro or aspirin). In such combination therapy, a compound of the invention may be administered prior to, or after administration of one or more other suitable anti-coagulant, anti-platelet, thrombolytic or other agents to boost or prolong desired anti-coagulation activity.

Compounds of this invention can be administered intranasally, orally or by injection, e.g., intramuscular, intraperitoneal, subcutaneous or intravenous injection, or by transdermal, intraocular or enteral means. Intravenous or parenteral administration includes e.g sub-cutaneous, intraperitoneal or intramuscular administration. Generally preferred is oral administration. The optimal dose can be determined by conventional means. Compounds of the present invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof.

Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Reference herein to a pharmaceutically acceptable counter-ion means a negatively or positively charged atom or molecule that is capable of forming an ionic bond with the compound. Examples of acceptable negatively charged atoms and molecules include chloride, bromide, iodide, acetate, citrate, oxalate, maleate, and the like. Illustrative pharmaceutically acceptable positively charged atoms and molecules include sodium, potassium, and ammonium ions. See *Remington's Pharmaceutical Sciences*, infra, for additional examples of pharmaceutically acceptable counter-ions.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degadable coatings, e.g., by microencapsulation, multiple coatings, etc.

See, in general, *Remington's Pharmaceutical Sciences*, (Mack Publishing Co., Easton Pa., (1980)), for a discussion of suitable administration formulations.

It will be appreciated that the actual preferred amounts of active compounds used in a given therapy will vary according to the specific compound being utilized, the particular compositions formulated, the mode of application, the particular site of administration, etc. Optimal administration for a given protocol of administration can be readily ascertained by those skilled in the art using conventional dosage determination tests conducted with regard to the foregoing guidelines. In general, a suitable effective dose of one or more compounds of Formula I will be in the range of about 0.01 to 100 milligrams per kilogram of bodyweight of recipient per day, preferably in the range of from about 0.01 to 20 to 50 milligrams per kilogram or bodyweight of recipient per day.

All documents mentioned herein are fully incorporated by reference in their entirety. The following non-limiting example is illustrative of the invention.

EXAMPLE 1

Screening

In this Example, purified human factors VIIa, IX and X, thrombin, and Russell's viper venom were obtained from Enzyme Research Laboratories Inc. Trypsin was from Boehringer Mannheim. Chromogenic substrates S-2222, S-2288, S-2238, and S-2765 were from DiaPharma Group Inc., and Spectrozyme FXa was from American Diagnostica Inc. Truncated recombinant human tissue factor (e.g. composed of 243 amino acids) is expressed in *E. coli* and purified by immunoaffinity chromatography. A preferred truncated recombinant human tissue factor lacks the cytoplasmic domain. Native human TF was extracted from human carcinoma cell line J82 with 50 mM Tris-HCl, pH 8.0, containing 0.1 M NaCl, 1 mM EDTA, 0.3% Triton X-100. Native TF from other sources is extracted with the same buffer from animal brain acetone powders. All other reagents were from Sigma.

The primary screening for compounds that inhibit tissue factor/factor VIIa (TF/VIIa) is based on TF/VIIa-dependent FX activation assay (See flow chart in FIG. 1 of the drawings). In this assay, the ability of TF/VIIa complex to activate FX is determined in two discontinuous stages. In the first stage (FX activation), the inactive FX is converted to an active enzyme form, FXa, by TF/VIIa in the presence of phospholipids and calcium. In the second stage (FXa activity assay), EDTA is added at indicated times to the FX activation mixture to chelate calcium, thus leading to the termination of FX→FXa conversion. Calcium is required for TF/VIIa activity. The activity of FXa is then measured by FXa-specific chromogenic substrates such as S-2222, S-2765, or Spectrozyme FXa In the primary screening, compounds from a previously prepared chemical library are first tested at relatively high concentrations (~0.833 mM) in TF/VIIa-dependent FX activation assay to identify hits of potential TF pathway antagonists (see FIG. 1). However, it is evident that the inhibition of TF/VIIa-dependent FX activation by a compound in this enzyme-coupled assay can be attributed to effects of the compound on TF/VIIa and/or FXa activities. Thus, secondary screening tests are designed to determine how inhibition takes place and the inhibition mechanism. In secondary screening experiments, effects of those compounds identified from primary screening are tested on catalytic activities of factor VIIa (FVIIa), factor IXa (FIXa), factor Xa (FXa), thrombin, Russell's viper venom (RVV), and trypsin. Additional tests such as the TF/VIIa-dependent factor IX activation assay and the prothrombin time (PT) assay were conducted to confirm desired activity, and secondary tests were conducted to further select compounds with good TF-antagonistic activity and that did not exhibit undesired activity.

A. Primary Screening: TF/VIIa-dependent FX Activation

Primary screening was done in duplicate in 96-well plates using the TF/VIIa-dependent FX activation assay. All compounds to be screened were dissolved in dimethyl sulfoxide (DMSO), other reagents were prepared or diluted in 25 mM HEPES-NaOH, 5 mM $CaCl_2$, 150 mM NaCl, 0.1% BSA, pH 7.5. For assays where TF was used, purified human recombinant TF (100 nM) was first lipidated with phosphatidylcholine (0.07 mg/ml) and phosphatidylserine (0.03 mg/ml) in 50 mM Tris-HCl, pH 7.5, 0.1% bovine serum albumin (BSA) for 30 minutes at 37° C. A stock solution of TF/VIIa complex was then prepared by combining equal volumes of 100 nM lipidated TF and 100 nM FVIIa. The complex was incubated at 37° C. for 30 minutes and then was aliquoted and stored at −70° C. for future uses.

For screening assays, 5 μl of each compound (about 10 mM in DMSO) or DMSO were placed in each well of a 96-well plate, followed by adding 45 μl of TF/VIIa complex (0.1 nM). The components in each well were mixed either with pipette tips or by shaking the plate on a Lab-Line titer plate shaker for 30 seconds. After 15 minutes incubation of the plate at a 37° C., 10 μl of human FX (180 nM) was added to each well and mixed as above. The plate was then incubated at 37° C. for 3 to 15 minutes, followed by addition of 10 μl of EDTA (400 mM in 144 mM HEPES, 864 mM NaCl, 0.576% BSA, pH adjusted to 7.5) to each well to terminate FX activation. Ten microliters of FXa substrate (5 mM Spectrozyme FXa, or 3.2 mM S-2765) was added to each well to measure FXa activity. The plate was mixed as above, and after about a 15 minute incubation at 37° C., FXa activity was quenched with 20 μl of 50% acetic acid. Absorbance at 405 nm was then read by an ELISA reader. The $OD_{405\ nm}$ values were transferred to a Microsoft Excel file and the percent inhibition of TF/VIIa-dependent FX activation was calculated by the following formula:

% Inhibition=100−(100×A/B)

where A and B are the OD values in the presence and absence of a compound, respectively. Any compound showing equivalent or greater than 70% inhibition of TF/VIIa-dependent FX activation was designated as a candidate for secondary screening test.

B. Secondary Screening

Those compounds identified in primary screening were retested in TF/VIIa-dependent FX activation assay at 10-, 50- or 100-fold diluted concentrations (see flow chart of FIG. 1 of the drawings). Compounds that failed to show significant inhibition at diluted concentrations, indicating that the inhibition is either non-specific or very weak, were not tested further. Compounds that inhibited TF/VIIa-dependent FX activation at diluted concentrations were further tested for their ability to inhibit activities of the following proteases, trypsin, RVV, thrombin, FXa, FVIIa, and FIXa. A target was to identify compounds that specifically prevent FX (and FIX) binding to TF/VIIa complex or interfere with TF and VIIa interaction so that FX (and FIX) activation is blocked. However, those compounds that have broad ability (non-specific) to inhibit several protease activities were not.further investigated. Compounds that met the specified criteria, that is, to inhibit TF/VIIa-dependent FX activation at lower concentrations (<0.1 mM) but without significant effects on protease activities, were selected, including compounds 1 through 19, whose structures are shown above, identified as strong TF antagonists and investigated further. Test data for those compounds are set forth in Table I of FIG. 2 of the drawings.

The invention has been described in detail with reference to preferred embodiments thereof. However, it will be appreciated that those skilled in the art, upon consideration of the disclosure, may make modification and improvements within the spirit and scope of the invention.

What is claimed is:

1. A method for treating a mammal susceptible to, suffering from, suspected of having or recovering from a disease impacted by tissue factor (TF), the method comprising administering to the mammal an effective amount of a compound or pharmaceutically acceptable salt thereof of the following Formulae I, II, IIIA, IV, IVA, V, VI, VIa, VII, VIII, IX, IXa, IXb, IXc, IXd, X, XI, XII or XIII:

$$Ar—(CXY)_m—(Het)_{0\ or\ 1}—(CX^1Y^1)_n—C(Z)_p—(T)_{3-p} \quad\quad I$$

Ar is optionally substituted carbocyclic aryl or optionally substituted heteroaryl;

Het is optionally substituted N, O or S;

each T is independently an amido, thioamido, carboxy, sulfinyl, sulfonyl, sulfonic, or nitro group;

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonly; or optionally substituted alkylamino;

m is an integer of from 0 to 4, and n is an integer of from 0 to 4; p is 1 or 2;

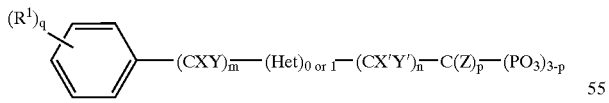

wherein X, Y, Het, T, X', Y', Z, m, and p are the same as defined in Formula I above;

wherein each $R^1$ is independently halogen; amino; hydroxy; nitro; carboxy; sulfhydryl; optionally substituted; optionally substituted; optionally substituted alkynyl; optionally substituted; optionally substituted; optionally substituted; optionally substituted alkylsulfonyl; optionally substituted; optionally substituted; optionally substituted carbocyclic aryl; or optionally substituted aralkyl;

q is an integer of from 0 to 5, or 3;

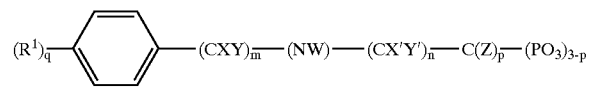

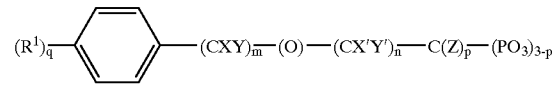

wherein in each of Formula III and IV, T, $R^1$, X, Y, X', Y', Z, q, m, n and p are the same as defined in Formulae I and II above; and W is hydrogen, optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted alkylamino; optionally substituted alkanoyl; optionally substituted carbocyclic aryl; or optionally substituted aralkyl;

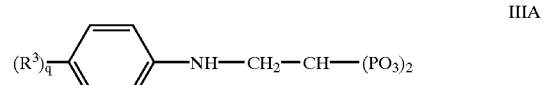

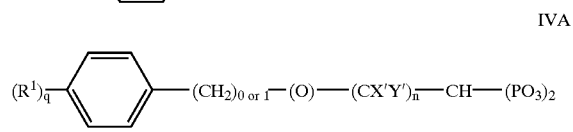

wherein T, $R^1$, X', Y', n and q are the same as defined in Formulae I and II above;

$$(R^2)_2N—(CXY)_{m1}—(Het)_{0\ or\ 1}—(CX^1Y^1)_n—C(Z)_p—(T)_{3-p} \quad\quad V$$

wherein each of X, Y, Het, X', Y', Z, T, n, g, p are each the same as defined in Formula I above; each $R^2$ is independently hydrogen alkyl, carbocyclic aryl; m1 is an integer of from 0 to 4;

$$Ar^1—(CXY)_{m2}—(Het)_{0\ or\ 1}—(CX^1Y^1)_n—C(Z)_p—(T)_{3-p} \quad\quad VI$$

wherein each of X, Y, X', Y', Z, n and p is defined as in Formula I above and $Ar^1$ represents a polycyclic aromatic group m2 is an integer of from 0 to 4;

$$(R^1)_{q1}—Ar^1—(CXY)_{m2}—(Het)_{0\ or\ 1}—(CX^1Y^1)_n—C(Z)_p—(T)_{3-p} \quad\quad VIa$$

wherein $R^1$ is the same as defined above in Formula II; and each of X, Y, X', Y', Z, g, n and p is defined as in Formula I above; m2 is the same as defined above in Formula VI; q1 is an integer from 0 to 7;

$$B—(CXY)_{m3}—(Het)_{0\ or\ 1}—(CX^1Y^1)_n—C(Z)_p—(T)_{3-p} \quad\quad VII$$

wherein B is an optionally substituted alicyclic or heteroalicyclic group; each of T, X, Y, X', Y', Z, n and p is defined as in Formula I above, m3 is an integer of from 0 to 4;

$$(R^1)_{q2}—B—(CXY)_{m3}—(Het)_{0\ or\ 1}—(CX^1Y^1)_n—C(Z)_p—(T)_{3-p} \quad\quad VIIa$$

wherein $R^1$ is the same as defined above in Formula II, each of X, Y, X', Y', Z, g, n and p is defined as in Formula I above, m3 is the same as defined above in Formula VIII, and q2 is an integer from 0 to 10;

In a more preferred embodiment of the Formula VIIa shown above, $R^1$ is hydroxyl; B is cyclohexyl or cyclopentyl; m3 and n are each 0; g is 1; Het is nitrogen; Z is hydrogen; q2 is 1; p is 2;

$$(T')_{q3}-D-(T'')_{q4} \qquad \text{VIII}$$

wherein T' and T" are each the same or different and are the same as defined for T in Formula I above; D is an optionally substituted imide, optionally with a $C_{1-6}$ alkylene linkage between D and either or both T' or T" groups;

$$(V)-(C=O)-(Het)_{0 \text{ or } 1}-Ar-(R^1)_{q5} \qquad \text{IX}$$

wherein V is a heteroalicyclic or heteroaromatic group having from 1 to 3 separate or fused rings, 5 to about 8 atoms in each ring, and 1–3 N, O or S atoms in each ring; Ar, Het are each the same as defined above in Formula I; $R^1$ is the same as defined above in Formula II; q5 is an integer from 0 to 5;

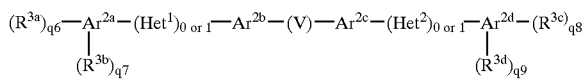

IXa wherein each of $R^{3a}$, $R^{3b}$, $R^{3c}$ and $R^{3d}$ is the same as the $R^1$ group defined in Formula II above with the proviso that each of $R^{3a}$, $R^{3b}$, $R^{3c}$ and $R^{3d}$ can be the same or different; $Het^1$ and $Het^2$ are each independently N, O or S the same or different; each of $Ar^{2a}$, $Ar^{2b}$, $Ar^{2c}$, and $Ar^{2d}$ is independently an optionally substituted carbocyclic aryl or optionally substituted heteroaryl group the same or different; V is the same as defined in Formula IX above; q6 is an integer from 0 to 5; q7 is the same as q6 with the proviso that q6+q7 is not greater than 5; q8 is an integer from 0 to 5; q9 is the same as q8 with the proviso that q7+q8 is not greater than 5;

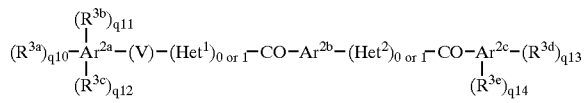

IXb wherein $R^{3e}$ is the same as the $R^1$ group defined in Formula II above, with the proviso that each of $R^{3a}$, $R^{3b}$, $R^{3c}$, $R^{3d}$ and $R^{3e}$ is the same or different; q10 is an integer from 0 to 5; q11 and q12 are each independently the same as q10 defined above with the proviso that q10+q11+q12 is not be greater than 5; q13 is an integer from 0 to 5; q14 is the same as q13 defined above with the proviso that q13+q14 is not greater than 5;

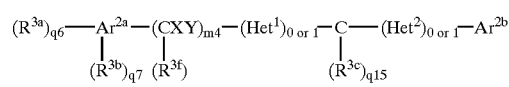

IXc wherein $R^{3f}$ is the same as $R^1$ as defined above in Formula II with the proviso that $R^{3f}$ can also be an optionally substituted cycloalkyl group having from about 5 to about 8 carbons, and $R^{3f}$ can be the same or different from each of $R^{3a}$, $R^{3b}$, and $R^{3c}$ as defined above; q7 is an integer from 0 to 5, with the proviso that q6+q7 in Formula IXc is not greater than 5; q15 is an integer from 0 to 2; m4 is an integer from 0 to 4;

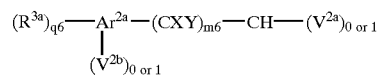

IXd wherein each of $(V^{2a})$ and $(V^{2b})$ is independently the same as V defined above in Formula IXd with the proviso that each of $(V^{2a})$ and $(V^{2b})$ can be the same or different and with the proviso that both $V^{2a}$ and $V^{2b}$ are not both 0; m6 is an integer from 0 to 4;

$$Ar^3-(CXY)_{m7}-(Het)_{0 \text{ or } 1}-(V) \qquad \text{X}$$

wherein $Ar^3$ is an optionally substituted carbocyclic aryl or heteroaryl group; each of X, Y, and Het is the same as defined above in Formula I with the proviso that X and Y can also join together to form a carbonyl group; m7 is an integer from 0 to 4; V is the same as defined above in Formula IXa;

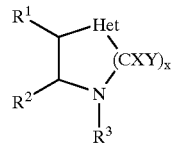

XI wherein $R^1$, $R^2$, $R^3$, X and Y each may be independently the same as defined for $R^1$ of Formula II above; or $R^1$ and $R^2$ of this Formula XI may be taken together to form a fused carbocyclic aryl, alicyclic, heteroalicyclic or heteroaromatic group having 1–3 fused or separate rings;

Het is oxygen, optionally substituted N, S, S(O) or S(O)$_2$;
and X is an in integer of from 1 to 4;

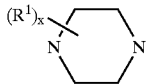
XII wherein each R$^1$ is independently the same as defined for R$^1$ of Formula II above; and x is an integer of from 1 to 10.

2. The method of claim 1 wherein the mammal is suffering from or susceptible to a cardiovascular disease, a blood coagulation disorder, a cell proliferation disorder, post-operative complication, an immune disorder, atheroselerosis, inflammation, or cancer.

3. The method of claim 1 wherein the mammal is suffering from, suspected of having, or recovering form a thrombosis.

4. The method of claim 1 wherein the mammal is suffering from, susceptible to, or recovering form a restenosis associated with an invasive medical procedure.

5. The method of claim 1 wherein the invasive medical procedure is angioplasty, endarterectomy, deployment of a stent, use of catheter, graft implantation or use of an arteriovenous shunt.

6. The method of claim 1 wherein the mammal is suffering from, at risk of developing, or recovering from a thrombaembolic condition associated with cardiovascular disease, an infectious disease, a neoplastic disease or use of a thrombolytic agent.

7. The method of claim 1 through 34 wherein at least one of an anti-platelet composition, thrombolytic composition or an anti-coagulant composition is administered in combination with a tissue factor blocking compound exhibiting an IC$_{50}$ of less than about 100 μM in a standard assay for increasing TF/VIIa-dependent factor X activation.

8. The method of claim 1 wherein the mammal is suffering from or susceptible to a thromoembolic disorder.

9. A method for treating a mammal susceptible to or suffering from a cardiovascular disease, a blood coagulation disorder, a cell proliferation disorder, an immune disorder, atheroselerosis, inflammation or cancer comprising administering to the mammal an effective amount of a compound or pharmaceutically acceptable salt thereof of the following Formulae I, II, III, IIIA, IV, IVA, V, VI, VIa, VII, VIII, IX, IXa, IXb, IXc, IXd, X, XI, XII or XIII:

$$Ar—(CXY)_m—(Het)_{0\ or\ 1}—(CX^1Y^1)_n—C(Z)_p—(T)_{3-p} \quad\quad I$$

Ar is optionally substituted carbocyclic aryl or optionally substituted heteroaryl;

Het is optionally substituted N, O or S;

each T is independently an amido, thioamido, carboxy, sulfinyl, sulfonyl, sulfonic, or nitro group;

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonly; or optionally substituted alkylamino;

m is an integer of from 0 to 4, and n is an integer of from 0 to 4; p is 1 or 2;

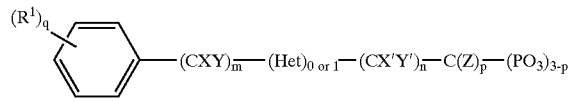
II wherein X, Y, Het, T, X', Y', Z, m, and p are the same as defined in Formula I above;

wherein each R$^1$ is independently halogen; amino; hydroxy; nitro; carboxy; sulfhydryl; optionally substituted; optionally substituted; optionally substituted alkynyl; optionally substituted; optionally substituted; optionally substituted; optionally substituted alkylsulfonyl; optionally substituted; optionally substituted; optionally substituted carbocyclic aryl; or optionally substituted aralkyl;

q is an integer of from 0 to 5, or 3;

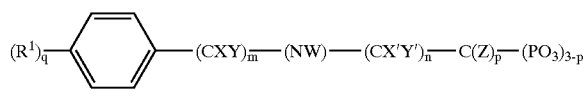
III

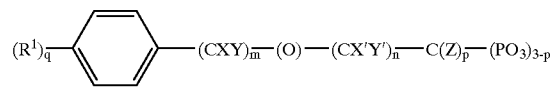
IV wherein in each of Formula III and IV, T, R$^1$, X, Y, X', Y', Z, q, m, n and p are the same as defined in Formulae I and II above; and W is hydrogen, optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted alkylamino; optionally substituted alkanoyl; optionally substituted carbocyclic aryl; or optionally substituted aralkyl;

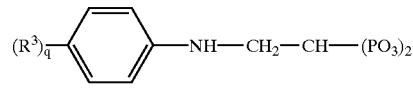
IIIA

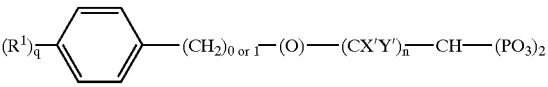
IVA wherein T, R$^1$, X', Y', n and q are the same as defined in Formulae I and II above;

$$(R^2)_2N—(CXY)_{m1}—(Het)_{0\ or\ 1}—CX^1Y^1)_n—C(Z)_p—(T)_{3-p} \quad\quad V$$

wherein each of X, Y, Het, X', Y', Z, T, n, g, p are each the same as defined in Formula I above; each R$^2$ is independently hydrogen alkyl, carbocyclic aryl; m1 is an integer of from 0 to 4;

$$Ar^1—(CXY)_{m2}—(Het)_{0\ or\ 1}—(CX^1Y^1)_n—C(Z)_p—(T)_{3-p} \quad\quad VI$$

wherein each of X, Y, X', Y', Z, n and p is defined as in Formula I above and Ar$^1$ represents a polycyclic aromatic group m2 is an integer of from 0 to 4;

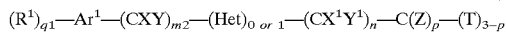
VIa wherein $R^1$ is the same as defined above in Formula II; and each of X, Y, X', Y', Z, g, n and p is defined as in Formula I above; m2 is the same as defined above in Formula VI; q1 is an integer from 0 to 7;

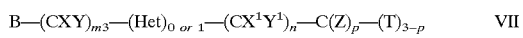
VII wherein B is an optionally substituted alicyclic or heteroalicyclic group; each of T, X, Y, X', Y', Z, n and p is defined as in Formula I above, m3 is an integer of from 0 to 4;

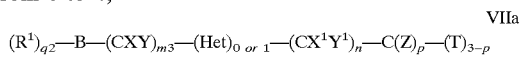
VIIa wherein $R^1$ is the same as defined above in Formula II, each of X, Y, X', Y', Z, g, n and p is defined as in Formula I above, m3 is the same as defined above in Formula VIII, and q2 is an integer from 0 to 10;

In a more preferred embodiment of the Formula VIIa shown above, $R^1$ is hydroxyl; B is cyclohexyl or cyclopentyl; m3 and n are each 0; g is 1; Het is nitrogen; Z is hydrogen; q2 is 1; p is 2;

$(T)_{q3}—D—(T'')_{q4}$  VIII wherein T' and T" are each the same or different and are the same as defined for T in Formula I above; D is an optionally substituted imide, optionally with a $C_{1-6}$ alkylene linkage between D and either or both T' or T" groups;

$(V)—(C=O)—(Het)_{0 \text{ or } 1}—Ar—(R^1)_{q5}$  IX wherein V is a heteroalicyclic or heteroaromatic group having from 1 to 3 separate or fused rings, 5 to about 8 atoms in each ring, and 1–3 N, O or S atoms in each ring; Ar, Het are each the same as defined above in Formula I; $R^1$ is the same as defined above in Formula II; q5 is an integer from 0 to 5;

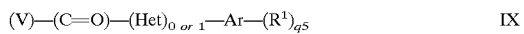
IXa wherein each of $R^{3a}$, $R^{3b}$, $R^{3c}$ and $R^{3d}$ is the same as the $R^1$ group defined in Formula II above with the proviso that each of $R^{3a}$, $R^{3b}$, $R^{3c}$ and $R^{3d}$ can be the same or different; $Het^1$ and $Het^2$ are each independently N, O or S the same or different; each of $Ar^{2a}$, $Ar^{2b}$, $Ar^{2c}$, and $Ar^{2d}$ is independently an optionally substituted carbocyclic aryl or optionally substituted heteroaryl group the same or different; V is the same as defined in Formula IX above; q6 is an integer from 0 to 5; q7 is the same as q6 with the proviso that q6+q7 is not greater than 5; q8 is an integer from 0 to 5; q9 is the same as q8 with the proviso that q7+q8 is not greater than 5;

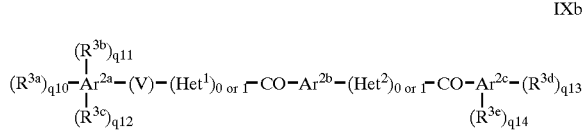
IXb wherein $R^{3e}$ is the same as the $R^1$ group defined in Formula II above, with the proviso that each of $R^{3a}$, $R^{3b}$, $R^{3c}$, $R^{3d}$ and $R^{3e}$ is the same or different; q10 is an integer from 0 to 5; q11 and q12 are each independently the same as q10 defined above with the proviso that q10+q11+q12 is not be greater than 5; q13 is an integer from 0 to 5; q14 is the same as q13 defined above with the proviso that q13+q14 is not greater than 5;

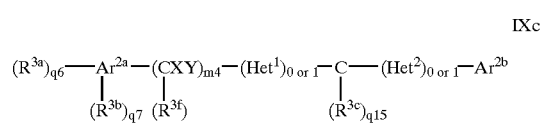
IXc wherein $R^{3f}$ is the same as $R^1$ as defined above in Formula II with the proviso that $R^{3f}$ can also be an optionally substituted cycloalkyl group having from about 5 to about 8 carbons, and $R^{3f}$ can be the same or different from each of $R^{3a}$, $R^{3b}$, and $R^{3c}$ as defined above; q7 is an integer from 0 to 5, with the proviso that q6+q7 in Formula IXc is not greater than 5; q15 is an integer from 0 to 2; m4 is an integer from 0 to 4;

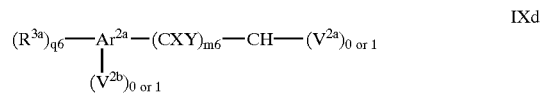
IXd wherein each of $(V^{2a})$ and $(V^{2b})$ is independently the same as V defined above in Formula IXd with the proviso that each of $(V^{2a})$ and $(V^{2b})$ can be the same or different and with the proviso that both $V^{2a}$ and $V^{2b}$ are not both 0; m6 is an integer from 0 to 4;

$Ar^3—(CXY)_{m7}—(Het)_{0 \text{ or } 1}—(V)$  X wherein $Ar^3$ is an optionally substituted carbocyclic aryl or heteroaryl group; each of X, Y, and Het is the same as defined above in Formula I with the proviso that X and Y can also join together to form a carbonyl group; m7 is an integer from 0 to 4; V is the same as defined above in Formula IXa;

XI wherein $R^1$, $R^2$, $R^3$, X and Y each may be independently the same as defined for $R^1$ of Formula II above; or $R^1$ and $R^2$ of this Formula XI may be taken together to form a fused carbocyclic aryl, alicyclic, heteroalicyclic or heteroaromatic group having 1–3 fused or separate rings;

Het is oxygen, optionally substituted N, S, S(O) or $S(O)_2$; and X is an in integer of from 1 to 4;

XII

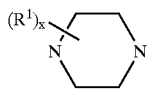

wherein each $R^1$ is independently the same as defined for $R^1$ of Formula II above; and x is an integer of from 1 to 10.

10. The method of claim 1 or 9 wherein the mammal is a human.

11. The method of claim 1 or 9 wherein the compound is selected from the group consisting of the following compounds 1 the 19 or a pharmaceutically acceptable salt thereof:

Compound 1

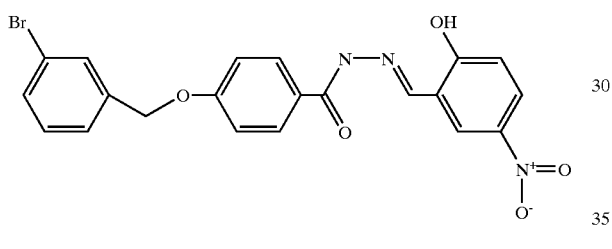

Compound 2

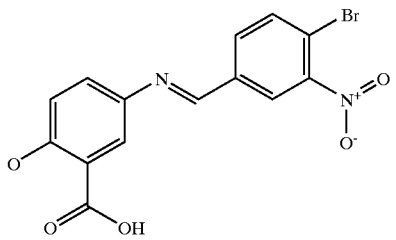

Compound 3

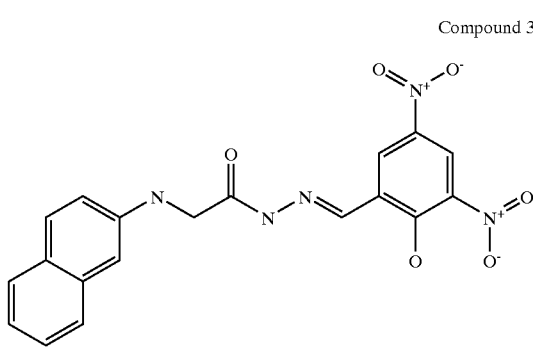

Compound 4

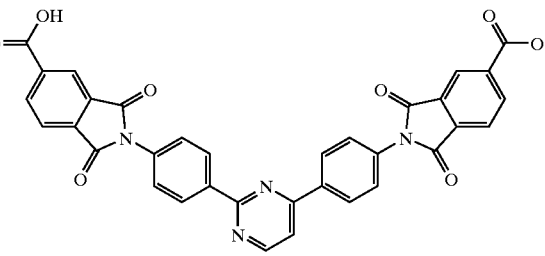

Compound 5

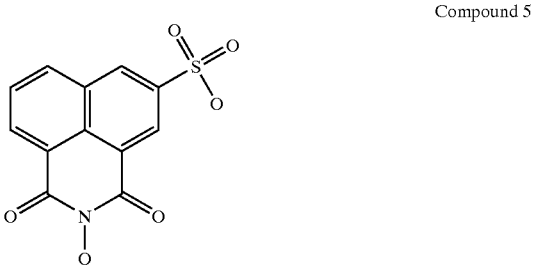

Compound 6

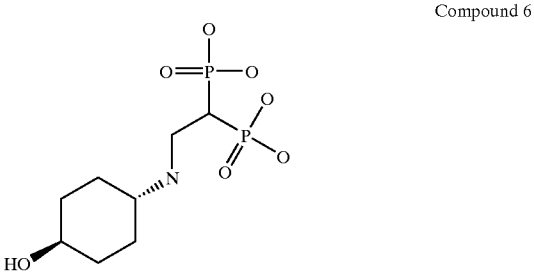

Compound 7

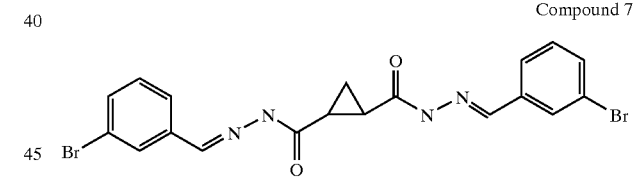

Compound 8

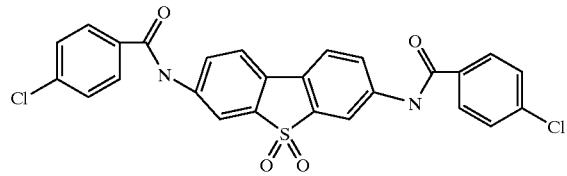

Compound 9

-continued

Compound 10
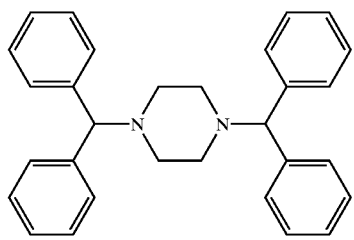

Compound 11
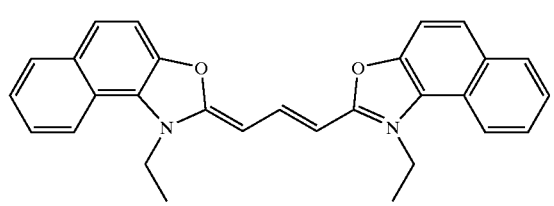

Compound 12
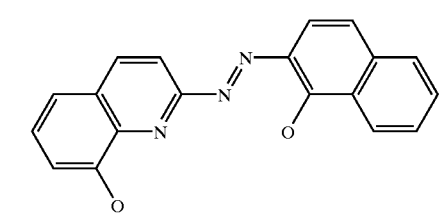

Compound 13
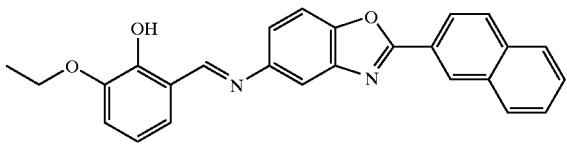

Compound 14
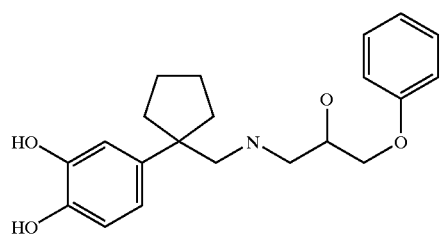

Compound 15
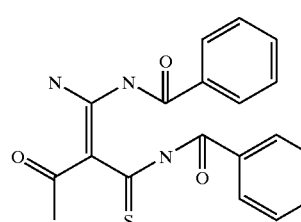

Compound 16
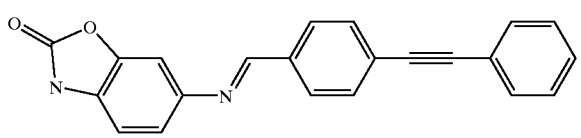

-continued

Compound 17
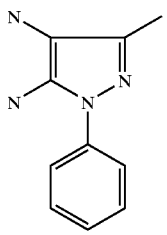

Compound 18
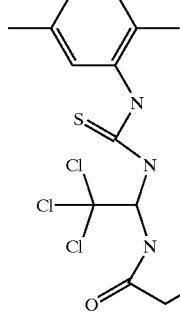

Compound 19
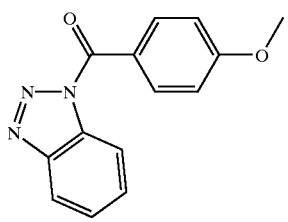

12. A compound of the following Formulae I, II, III, IIIA, IV, IVA, V, VI, VIa, VII, VIII, IX, IXa, IXb, IXc, IXd, X, XI, XII or XIII:

$$Ar-(CXY)_m-(Het)_{0\text{ or }1}-(CX^1Y^1)_n-C(Z)_p-(T)_{3-p} \quad\quad I$$

Ar is optionally substituted carbocyclic aryl or optionally substituted heteroaryl;

Het is optionally substituted N, O or S;

each T is independently an amido, thioamido, carboxy, sulfinyl, sulfonyl, sulfonic, or nitro group;

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonly; or optionally substituted alkylamino;

m is an integer of from 0 to 4; n is an integer of from 0 to 4; p is 1 or 2;

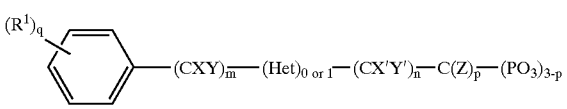

wherein X, Y, Het, T, X', Y', Z, m, and p are the same as defined in Formula I above;

wherein each $R^1$ is independently halogen; amino; hydroxy; nitro; carboxy; sulfhydryl; optionally substituted; optionally substituted; optionally substituted alkynyl; optionally substituted; optionally substituted; optionally substituted; optionally substituted alkylsulfonyl; optionally substituted; optionally substituted; optionally substituted carbocyclic aryl; or optionally substituted aralkyl;

q is an integer of from 0 to 5, or 3;

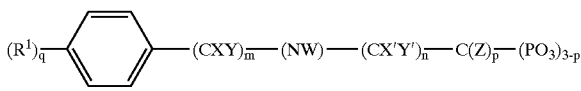

III

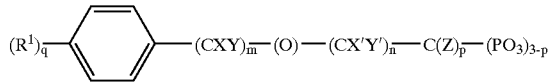

IV wherein in each of Formula III and IV, T, $R^1$, X, Y, X', Y', Z, q, m, n and p are the same as defined in Formulae I and II above; and W is hydrogen, optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted alkylamino; optionally substituted alkanoyl; optionally substituted carbocyclic aryl; or optionally substituted aralkyl;

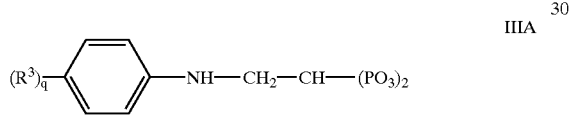

IIIA

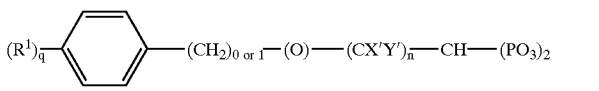

IVA wherein T, $R^1$, X', Y', n and q are the same as defined in Formulae I and II above;

$$(R^2)_2N-(CXY)_{m1}-(Het)_{0\ or\ 1}-(CX^1Y^1)_n-C(Z)_p-(T)_{3-p} \quad V$$

wherein each of X, Y, Het, X', Y', Z, T, n, g, p are each the same as defined in Formula I above; each $R^2$ is independently hydrogen alkyl, carbocyclic aryl; m1 is an integer of from 0 to 4;

$$Ar^1-(CXY)_{m2}-(Het)_{0\ or\ 1}-(CX^1Y^1)_n-C(Z)_p-(T)_{3-p} \quad VI$$

wherein each of X, Y, X', Y', Z, n and p is defined as in Formula I above and $Ar^1$ represents a polycyclic aromatic group m2 is an integer of from 0 to 4;

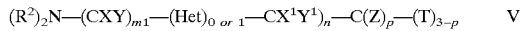 VIa wherein $R^1$ is the same as defined above in Formula II; and each of X, Y, X', Y', Z, g, n and p is defined as in Formula I above; m2 is the same as defined in Formula VI; q1 is an integer from 0 to 7;

$$B-(CXY)_{m3}-(Het)_{0\ or\ 1}-(CX^1Y^1)_n-C(Z)_p-(T)_{3-p} \quad VII$$

wherein B is an optionally substituted alicyclic or heteroalicyclic group; each of T, X, Y, X', Y', Z, n and p is defined as in Formula I above, m3 is an integer of from 0 to 4;

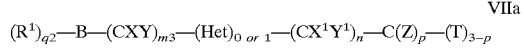 VIIa wherein $R^1$ is the same as defined above in Formula II, each of X, Y, X', Y', Z, g, n and p is defined as in Formula I above, m3 is the same as defined above in Formula VIII, and q2 is an integer from 0 to 10;

In a more preferred embodiment of the Formula VIIa shown above, $R^1$ is hydroxyl; B is cyclohexyl or cyclopentyl; m3 and n are each 0; g is 1; Het is nitrogen; Z is hydrogen; q2 is 1; p is 2;

$$(T')_{q3}-D-(T'')_{q4} \quad VIII$$

wherein T' and T'' are each the same or different and are the same as defined for T in Formula I above; D is an optionally substituted imide, optionally with a $C_{1-6}$ alkylene linkage between D and either or both T' or T'' groups;

$$(V)-(C=O)-(Het)_{0\ or\ 1}-Ar-(R^1)_{q5} \quad IX$$

wherein V is a heteroalicyclic or heteroaromatic group having from 1 to 3 separate or fused rings, 5 to about 8 atoms in each ring, and 1–3 N, O or S atoms in each ring; Ar, Het are each the same as defined above in Formula I; $R^1$ is the same as defined above in Formula II; q5 is an integer from 0 to 5;

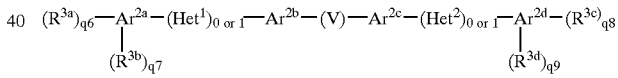 IXa wherein each of $R^{3a}$, $R^{3b}$, $R^{3c}$ and $R^{3d}$ is the same as the $R^1$ group defined in Formula II above with the proviso that each of $R^{3a}$, $R^{3b}$, $R^{3c}$ and $R^{3d}$ can be the same or different; $Het^1$ and $Het^2$ are each independently N, O or S the same or different; each of $Ar^{2a}$, $Ar^{2b}$, $Ar^{2c}$, and $Ar^{2d}$ is independently an optionally substituted carbocyclic aryl or optionally substituted heteroaryl group the same or different; V is the same as defined in Formula IX above; q6 is an integer from 0 to 5; q7 is the same as q6 with the proviso that q6+q7 is not greater than 5; q8 is an integer from 0 to 5; q9 is the same as q8 with the proviso that q7+q8 is not greater than 5;

IXb

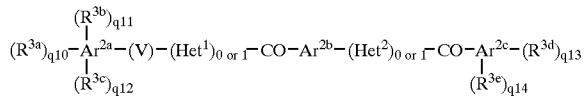

wherein $R^{3e}$ is the same as the $R^1$ group defined in Formula II above, with the proviso that each of $R^{3a}$, $R^{3b}$, $R^{3c}$, $R^{3d}$ and $R^{3e}$ is the same or different; q10 is an integer from 0 to 5; q11 and q12 are each independently the same as q10 defined above with the proviso that q10+q11+q12 is not be greater than 5; q13 is an integer from 0 to 5; q14 is the same as q13 with the proviso that q13+q14 is not greater than 5;

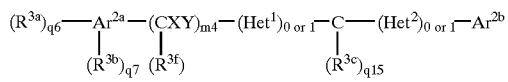

IXc wherein $R^{3f}$ is the same as $R^1$ as defined above in Formula II with the proviso that $R^{3f}$ can also be an optionally substituted cycloalkyl group having from about 5 to about 8 carbons, and $R^{3f}$ can be the same or different from each of $R^{3a}$, $R^{3b}$, and $R^{3c}$ as defined above; q7 is an integer from 0 to 5, with the proviso that q6+q7 in Formula IXc is not greater than 5; q15 is an integer from 0 to 2; m4 is an integer from 0 to 4;

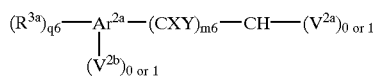

IXd wherein each of $(V^{2a})$ and $(V^{2b})$ is independently the same as V defined above in Formula IXd with the proviso that each of $(V^{2a})$ and $(V^{2b})$ can be the same or different and with the proviso that both $V^{2a}$ and $V^{2b}$ are not both 0; m6 is an integer from 0 to 4;

$$Ar^3—(CXY)_{m7}—(Het)_{0\ or\ 1}—(V) \qquad X$$

wherein $Ar^3$ is an optionally substituted carbocyclic aryl or heteroaryl group; each of X, Y, and Het is the same as defined above in Formula I with the proviso that X and Y can also join together to form a carbonyl group; m7 is an integer from 0 to 4; V is the same as defined above in Formula IXa;

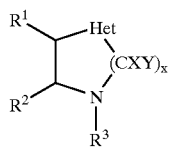

XI wherein $R^1$, $R^2$, $R^3$, X and Y each may be independently the same as defined for $R^1$ of Formula II above; or $R^1$ and $R^2$ of this Formula XI may be taken together to form a fused carbocyclic aryl, alicyclic or heteroalicyclic or heteroaromatic group having 1–3 fused or separate rings;
Het is oxygen, optionally substituted N, S, S(O) or S(O)$_2$; and X is an in integer of from 1 to 4;

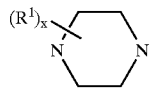

XII wherein each $R^1$ is independently the same as defined for $R^1$ of Formula II above; and x is an integer of from 1 to 10; or
a pharmaceutically acceptable salt thereof.

13. The method of claim 12 wherein the compound is selected from the group consisting of the following compounds 1 the 19 or a pharmaceutically acceptable salt thereof:

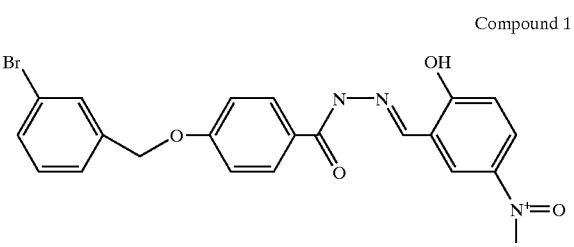

Compound 1

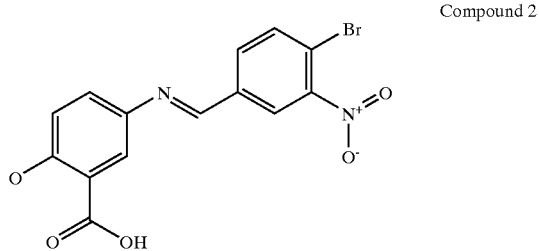

Compound 2

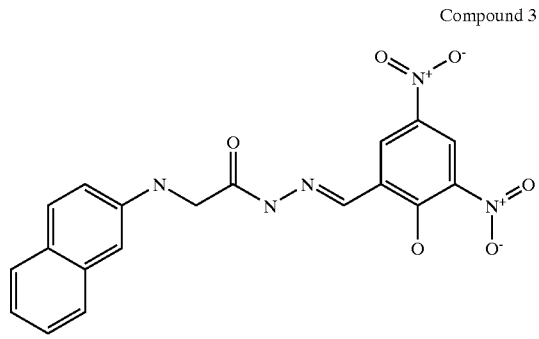

Compound 3

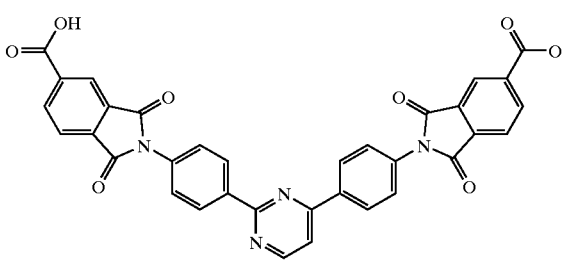

Compound 4

-continued

Compound 5

Compound 6

Compound 7

Compound 8

Compound 9

Compound 10

Compound 11

-continued

Compound 12

Compound 13

Compound 14

Compound 15

Compound 16

Compound 17

Compound 18
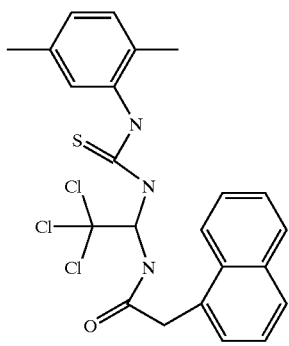
Compound 19
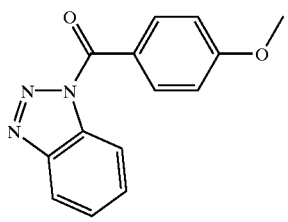
14. A pharmaceutical composition comprising a compound of claim 12 or 13 and a pharmaceutically acceptable carrier.
* * * * *

UNITED STATES PATENT AND TRADEMARK OFFICE
CERTIFICATE OF CORRECTION

PATENT NO. : 6,608,066 B1 Page 1 of 1
APPLICATION NO. : 09/698673
DATED : August 19, 2003
INVENTOR(S) : Jiao et al.

It is certified that error appears in the above-identified patent and that said Letters Patent is hereby corrected as shown below:

In claim 11, column 33 at line 22, please replace "1 the 19" with

--1 through 19--.

In claim 14, column 44 at line 14, please replace "claim 12 or 13" with

--claim 12 or 13--.

Signed and Sealed this

Twenty-eighth Day of August, 2007

JON W. DUDAS
*Director of the United States Patent and Trademark Office*